(12) United States Patent
Wischik et al.

(10) Patent No.: US 10,842,796 B2
(45) Date of Patent: *Nov. 24, 2020

(54) TREATMENT OF DEMENTIA

(71) Applicant: WisTa Laboratories Ltd., Singapore (SG)

(72) Inventors: Claude Michel Wischik, Aberdeen (GB); Björn Olaf Schelter, Aberdeen (GB); Damon Jude Wischik, Cambridge (GB); John Mervyn David Storey, Old Aberdeen (GB)

(73) Assignee: WisTa Laboratories Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/329,611

(22) PCT Filed: Aug. 25, 2017

(86) PCT No.: PCT/EP2017/071437
§ 371 (c)(1),
(2) Date: Feb. 28, 2019

(87) PCT Pub. No.: WO2018/041739
PCT Pub. Date: Mar. 8, 2018

(65) Prior Publication Data
US 2019/0192530 A1 Jun. 27, 2019

(30) Foreign Application Priority Data
Sep. 1, 2016 (GB) .................................. 1614834.8

(51) Int. Cl.
| *A61K 31/5415* | (2006.01) |
| *A61K 45/06* | (2006.01) |
| *A61K 9/48* | (2006.01) |
| *A61K 31/136* | (2006.01) |
| *A61K 31/165* | (2006.01) |
| *A61K 31/445* | (2006.01) |
| *A61K 31/55* | (2006.01) |
| *A61K 9/20* | (2006.01) |

(52) U.S. Cl.
CPC ........ *A61K 31/5415* (2013.01); *A61K 9/4816* (2013.01); *A61K 31/136* (2013.01); *A61K 31/165* (2013.01); *A61K 31/445* (2013.01); *A61K 31/55* (2013.01); *A61K 45/06* (2013.01); *A61K 9/2054* (2013.01)

(58) Field of Classification Search
CPC .................................................. A61K 31/5415
USPC ....................................................... 514/224.8
See application file for complete search history.

(56) References Cited

U.S. PATENT DOCUMENTS 9,283,230 B2 * 3/2016 Clunas ................. C07D 279/20

FOREIGN PATENT DOCUMENTS

| WO | WO 2003/101458 A1 | 12/2003 | |
| WO | WO 2007/110627 A2 | 10/2007 | |
| WO | WO 2007/110630 A1 | 10/2007 | |
| WO | WO-2007110630 A1 * | 10/2007 | ......... A61K 31/5415 |
| WO | WO 2011/036561 A2 | 3/2011 | |
| WO | WO 2012/107706 A1 | 8/2012 | |

OTHER PUBLICATIONS

Feldman et al., A phase 3 trial of the tau and TDP-43 aggregation inhibitor, leuco-methylthioninium-bis (hydromethanesulfonate) (LMTM), for behavioural variant frontotemporal dementia (bvFTD). J Neurochemistry. Jul. 18, 2016;138(1):255.
Tsai et al., Therapy and clinical trials in frontotemporal dementia:past, present, and future. J Neurochem. Aug. 2016;138 Suppl 1:211-21. doi:10.1111/jnc.13640. Epub Jun. 15, 2016.
Tsai et al., Treatment of frontotemporal dementia. Curr Treat Options Neurol. Nov. 2014;16(11):319. doi: 10.1007/s11940-014-0319-0.
Yamashita et al., Methylene blue and dimebon inhibit aggregation of TDP-43 in cellular models. FEBS Lett. Jul. 21, 2009;583(14):2419-24. doi:10.1016/j.febslet.2009.06.042. Epub Jun. 26, 2009.
PCT/EP2017/071437, Nov. 24, 2017, International Search Report and Written Opinion.

* cited by examiner

*Primary Examiner* — Kevin E Weddington
(74) *Attorney, Agent, or Firm* — Wolf, Greenfield & Sacks, P.C.

(57) ABSTRACT

The invention describes improved treatments for Frontotemporal dementia based on the use of a methylthioninium compound in combination with a compound which directly modifies synaptic neurotransmission in the brain, such as a symptomatic Alzheimer's disease treatment (e.g. acetylcholinesterase and/or memantine).

12 Claims, 11 Drawing Sheets

TREATMENT OF DEMENTIA

CROSS-REFERENCE TO RELATED APPLICATIONS

This Application is a National Stage filing under 35 U.S.C. 371 of International Patent Application Serial No. PCT/EP2017/071437, filed Aug. 25, 2017, which claims priority to Great Britain Application No. 1614834.8, filed Sep. 1, 2016. The contents of these applications are incorporated herein by reference in their entirety.

TECHNICAL FIELD

The present invention relates generally to methods and materials for use in the treatment or prophylaxis of diseases of frontotemporal dementia disease.

BACKGROUND ART

FTD and FTLD Syndromes

Frontotemporal dementia (FTD) is a clinical concept describing certain insidious onset, inexorably progressive, neurodegenerative conditions, with peak onset in late middle age. There is often a positive family history of similar disorders in a first degree relative.

Behavioural variant FTD is characterised by early prominent change in social and interpersonal function, often accompanied by repetitive behaviours and changes in eating pattern.

In semantic dementia there are prominent word finding problems, despite otherwise fluent speech, with degraded object knowledge and impaired single word comprehension on cognitive assessment.

Progressive non-fluent aphasia presents with a combination of motor speech problems and grammatical deficits.

FTD as a clinical concept can be backed up by subsequent pathology analysis, and this has led to the use of 'frontotemporal lobar degeneration' (FTLD) to describe the discernible underlying pathology underlying FTD, which is largely divided between tauopathy and TAR DNA-binding protein 43 (TDP-43) proteinopathy (Ferrari et al. (2014) Frontotemporal dementia and its subtypes: a genome-wide association study. Lancet Neurol. 13:686-699).

Treatments for FTD

Although significant advances have been made in recent years regarding diagnostic criteria, clinical assessment instruments, neuropsychological tests, cerebrospinal fluid biomarkers, and brain imaging techniques, to date, there is no specific pharmacological treatment for FTLD. Some evidence has been provided for serotonin reuptake inhibitors to reduce behavioral disturbances (Riedl, L, Mackenzie, I R, Forstl, H, Kurz, A, Diehl-Schmid, J (2014) Frontotemporal lobar degeneration: current perspectives. Neuropsychiatric Disease and Treatment 10:297-3).

Methylthioninium (MT) acts as a tau aggregation inhibitor (TAI) in vitro, dissolves PHFs from Alzheimer's disease brain tissue, and reduces tau pathology and associated behavioural deficits in transgenic mouse tau models at brain concentrations consistent with human oral dosing (Wischik et al, (1996) PNAS 92, 11213-11218; WO96/30766; Harrington et al., J Biol Chem, 2015, 290 10862-10875). Furthermore MT has also been shown to inhibit other disease-associated protein aggregation, including TDP-43 (see e.g. Yamashita et al. (2009) FEBS Letters 583:2419-2424).

Because of their activity in respect of tau aggregation and TDP-43 aggregation, MT-based compounds have been suggested for the treatment of FTD (see WO2007/110630; WO2007/110627; WO2009/044127; WO2012/107706).

Specifically, WO96/30766 describes MT-containing compounds for use in the treatment and prophylaxis of various "tauopathy" diseases. One example compound was methylthioninium chloride ("MTC") commonly known as methylene blue, which is the chloride salt of the oxidized form of methylthioninium (MT) i.e. $MT^+$.

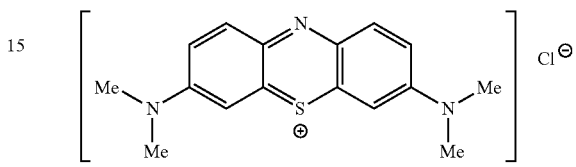

MT is a redox molecule and, depending on environmental conditions (e.g., pH, oxygen, reducing agents), exists in equilibrium between a reduced [leucomethylthioninium (LMT)] and an oxidized form ($MT^+$).

MTC, a phenothiazin-5-ium salt, may be considered to be an "oxidized form" in relation to the corresponding 10H-phenothiazine compound, N,N,N',N'-tetramethyl-10H-phenothiazine-3,7-diamine, which may be considered to be a "reduced form":

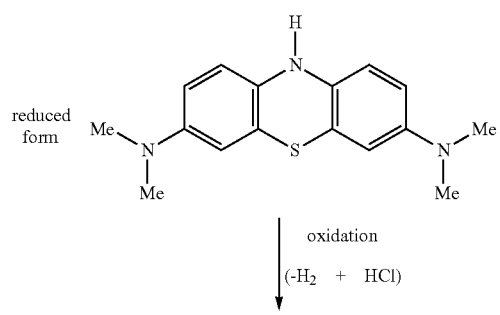

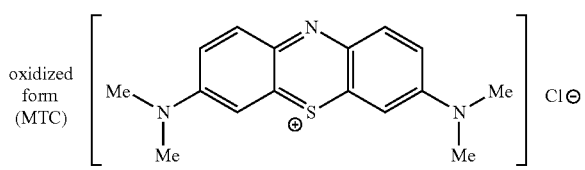

The "reduced form" (or "leuco form") is known to be unstable and can be readily and rapidly oxidized to give the corresponding "oxidized" form.

However since it is believed to be the reduced form of MT that is taken up by cells, it has been proposed to administer a reduced form to patients.

WO2007/110627 disclosed certain 3,7-diamino-10H-phenothiazinium salts, effective as drugs or pro-drugs for the treatment of diseases including tauopathies. These compounds are also in the "reduced" or "leuco" form when considered in respect of MTC. These leucomethylthioninium compounds were referred to as "LMTX" salts, and included (amongst others) the following salt:

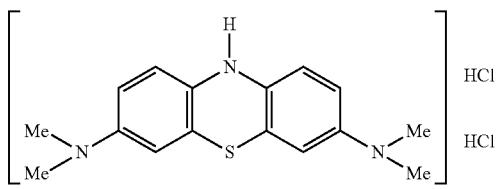

WO2012/107706 described other LMTX salts having superior properties to the LMTX salts listed above, including leuco-methylthioninium bis(hydromethanesulfonate) (LMTM):

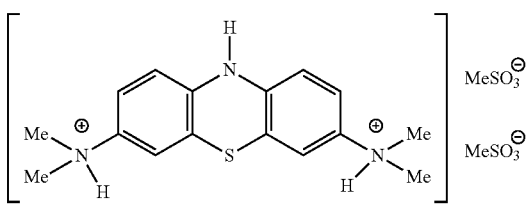

WO2012/107706 describes these salts for treating FTLD pathologies.

Nevertheless, in view of their importance in public health, it can be seen that further or improved treatments for FTD would provide a contribution to the art.

DISCLOSURE OF THE INVENTION

The present inventors have conducted a phase 3 clinical trial investigating the treatment of an FTD disease using LMTM.

The results indicate that even a relatively low dose of the MT compound (which was used in the trial as a control) may show benefit in FTD, as compared to the cognitive decline seen in historical controls.

Furthermore, unexpectedly, the results indicate strong interaction effects when MT is co-medicated with Alzheimer's Disease (AD) treatments which modify synaptic neurotransmission in the brain. There appeared significant cognitive benefits in FTD patients taking MT in combination with such AD treatments (e.g. acetylcholinesterase inhibitors and/or memantine) compared to MT alone.

There have previously been a few small trials of drugs used to treat AD (donepezil, rivastigmine, galantamine and memantine) undertaken in people with FTD. These have had mixed results. In some cases, these drugs made people's symptoms worse. Although these treatments are sometimes used 'off label' in patients with FTD diseases, they are not licensed for use in FTD and are not widely prescribed (see "What is frontotemporal dementia (FTD)?" factsheet 4041p issued by the Alzheimer's society April 2016).

Although the underlying basis for the beneficial combination is not fully understood, nevertheless the findings described herein have implications for improved MT-based treatments for FTLD syndromes.

Thus in one aspect of the invention there is provided a method of treatment of an FTLD syndrome in a subject, which method comprises administering to said subject a methylthioninium (MT)-containing compound in combination with a treatment which modifies synaptic neurotransmission in the brain.

The treatments described herein are therapeutic treatments. However, as explained hereinafter, also provided are corresponding methods of prophylactic treatment of FTLD syndromes. It will be understood that the disclosure of therapeutic treatments herein applies mutatis mutandis to prophylactic treatment, unless context requires otherwise.

The term "treatment," as used herein in the context of treating a condition (here: an FTLD syndrome) pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition.

The Examples hereinafter teach both cognitive assessments and physical (imaging) methodologies for judging the severity or rate of decline or improvement of FTLD syndromes.

The term "therapeutically-effective amount," where used herein, pertains to that amount of an agent used in the practice of the combination methodologies of the invention which is effective for producing some desired therapeutic effect, commensurate with a reasonable benefit/risk ratio, when administered in accordance with a desired treatment regimen. The present inventors have demonstrated that a therapeutically-effective amount of an MT compound in respect of FTLD disease may be lower than was hitherto understood in the art, and also that the therapeutic effect of the MT compound is enhanced by the use of AD treatments.

As explained above the invention also embraces treatment as a prophylactic measure. For example the invention provides a method of prophylactic treatment of an FTLD syndrome in a subject, which method comprises administering to said subject a methylthioninium (MT)-containing compound in combination with a treatment which directly modifies synaptic neurotransmission in the brain.

The term "prophylactically effective amount," where used herein, pertains to that amount of a compound of the invention, or a material, composition or dosage from comprising said compound, which is effective for producing some desired prophylactic effect, commensurate with a reasonable benefit/risk ratio, when administered in accordance with a desired treatment regimen.

"Prophylaxis" in the context of the present specification should not be understood to circumscribe complete success i.e. complete protection or complete prevention. Rather prophylaxis in the present context refers to a measure which is administered in advance of detection of a symptomatic condition with the aim of preserving health by helping to delay, mitigate or avoid that particular condition.

The invention also provides use of a first compound, which is an MT compound, in a method of treatment of an FTLD syndrome in a subject in a treatment regimen which additionally comprises treatment with a second compound, which second compound directly modifies synaptic neurotransmission in the brain of the subject.

The invention also provides an MT compound and a compound which directly modifies synaptic neurotransmission in the brain for use in the combination methods described herein.

The invention also provides use of a first compound which is an MT compound in combination with a second compound, which second compound directly modifies synaptic neurotransmission in the brain of the subject, in the manufacture of a medicament for treatments as described herein.

The invention also provides containers including:
(ii) a compound which directly modifies synaptic neurotransmission in the brain and\or
(ii) an MT compound;
(iii) a label or instructions indicate a combination treatment as described herein.

The invention also provides novel combination dosage forms comprising (i) a compound which directly modifies synaptic neurotransmission in the brain and (ii) an MT compound.

Some of these aspects and embodiments, and other aspects and embodiments of the invention, will now be described in more detail:

Combination Treatments

"Combination" treatments and therapies are those in which two or more treatments or therapies are combined, for example sequentially or simultaneously, for treating a single indication (here: an FTLD syndrome) in a subject.

The present invention concerns a combination of an MT compound as active ingredient (which is to say that it is present to provide the recited therapeutic effect) and a different, additional, active therapeutic compound, which additional therapeutic directly modifies synaptic neurotransmission in the brain—for example an AD symptomatic treatment which is one or both of an acetylcholinesterase inhibitor or an N-methyl-D-aspartate receptor [NMDA] antagonist. Any such additional treatment may be termed an "AD treatment" for brevity herein. Such treatments are described in more detail hereinafter.

In combination treatments, the agents (i.e., an MT compound as described herein plus the AD treatment) may be administered simultaneously, separately, or sequentially, and may be administered in individually varying dose schedules and via different routes. For example, when administered sequentially, the agents can be administered at closely spaced intervals (e.g., over a period of 5-10 minutes) or at longer intervals (e.g., less than, equal to, or more than, 1, 2, 3, 4 or more hours apart, or even longer periods apart where required e.g. up to 12 or 24 hours apart).

An example of a combination treatment of the invention would be where the subject is regularly administered, for purpose of treatment of an FLTD syndrome, an agent which is an MT-containing compound with an agent which is an acetylcholinesterase inhibitor and\or an N-methyl-D-aspartate receptor antagonist. The administration of each may be chronic—for example taking at least one administration of each type of medication once, twice or three times daily over the medium to long term. The administration may be staggered e.g. taking the compounds at different times of the day, or on alternate days.

Thus one aspect of the present invention provides a method of combination treatment of an FTLD syndrome in a subject, which method comprises administering to said subject a methylthioninium (MT)-containing compound in combination with a compound which directly modifies synaptic neurotransmission in the brain.

The invention also provides a method of enhancing the therapeutic effectiveness of an MT compound in the treatment of an FTLD syndrome in a subject, the method comprising administering to the subject a compound which directly modifies synaptic neurotransmission in the brain of the subject.

Another aspect provides use of a compound which directly modifies synaptic neurotransmission in the brain of a subject to enhance the therapeutic effectiveness of an MT compound in the treatment of an FTLD syndrome in the subject.

The invention also provides use of an MT compound in a method of treatment of an FTLD syndrome in a subject in a regimen which additionally comprises treatment with a compound which directly modifies synaptic neurotransmission in the brain of the subject.

In these embodiments the subject is preferably pre-treated with the AD treatment prior to commencement of the treatment with the MT compound.

Another aspect of the present invention pertains to an MT containing compound and a compound which directly modifies synaptic neurotransmission in the brain for use in a combination method of treatment of an FTLD syndrome in a subject.

As described above the compounds may be used simultaneously, separately or sequentially.

Another aspect of the present invention pertains to a compound which directly modifies synaptic neurotransmission in the brain of the subject for use in a method of enhancing the therapeutic effectiveness of an MT compound in the treatment of an FTLD syndrome in a subject.

In this embodiment the subject is preferably pre-treated with the AD treatment prior to the MT compound.

Another aspect of the present invention pertains to use of an MT compound as described herein in combination with a compound which directly modifies synaptic neurotransmission in the brain of the subject, in the manufacture of a medicament for treatment of an FTLD syndrome in a subject.

Another aspect of the present invention pertains to use of an MT compound as described herein, in the manufacture of a medicament for use in the treatment of an FTLD syndrome in a subject, which treatment further comprises use of a compound which directly modifies synaptic neurotransmission in the brain of the subject.

Another aspect of the present invention pertains to use of a compound which directly modifies synaptic neurotransmission in the brain, in the manufacture of a medicament for use in the treatment of an FTLD syndrome in the subject, which treatment further comprises use of an MT compound described herein.

To put it another way, in each case the medicament is for use in a combination treatment. As described above the compounds may be used simultaneously, separately or sequentially in the treatment.

Thus another aspect of the present invention pertains to use of an MT compound as described herein, in the manufacture of a medicament for use in the treatment of an FTLD syndrome in a subject, wherein the MT compound is for use with a compound which directly modifies synaptic neurotransmission in the brain of the subject.

And another aspect of the present invention pertains to use of a compound which directly modifies synaptic neurotransmission in the brain, in the manufacture of a medicament for use in the treatment of an FTLD syndrome in the subject, wherein the compound which directly modifies synaptic neurotransmission in the brain of the subject is for use with the MT compound as described herein.

And another aspect of the present invention pertains to use of a compound which directly modifies synaptic neurotransmission in the brain of the subject in the preparation of a medicament for enhancing the therapeutic effectiveness of an MT compound in the treatment of an FTLD syndrome in a subject.

Subjects, Patients and Patient Groups

In the various aspects of the present invention the subject or patient is an animal, preferably a human.

In preferred therapeutic embodiments, the subject/patient is a human who has been diagnosed as having an FTLD syndrome. Generally the subject/patient is a human who does not have AD (i.e. one for whom AD has been excluded as a diagnosis). FTLD syndromes are described in more detail below. Diagnosis of FTLD syndromes can be performed by physicians by methods well known to those skilled in the art.

The patient may optionally be one which has failed to respond to other FTLD treatments.

For prophylactic embodiments, the subject may be one assessed as being susceptible to an FTLD syndrome—for example based on familial or genetic or other data. As explained herein, FTLD syndromes often show such familial or genetic links.

As explained above, in the present invention, the subject or patient group may be one which is already being treated with a compound which directly modifies synaptic neurotransmission in the brain, prior to treatment with the MT compound. For example the subject or patient group may have historically received the AD treatment at least 1, 2, 3, 4, 5, 6, 7, 8, 12, or 16 weeks prior to treatment with an MT compound according to the present invention e.g. at least 3 months before.

Compounds which Modify Synaptic Neurotransmission

The present invention is based on combination treatments including therapeutic compounds which directly modify synaptic neurotransmission in the brain. Such compounds have previously been approved for treatment of AD, although their benefit in FTLD has not previously been demonstrated.

Five examples of these compounds have been approved for AD (Casey, David A., Demetra Antimisiaris, and James O'Brien. "Drugs for Alzheimer's disease: are they effective?." *Pharmacy and Therapeutics* 35.4 (2010): 208). Four of these medications are classified together as acetylcholinesterase inhibitors (AChEIs)—these include tacrine, donepezil, rivastigmine, and galantamine.

Tacrine has subsequently been excluded because it is associated with significant liver toxicity.

The fifth AD drug, memantine, opposes glutamate activity by blocking NMDA receptors.

The four drugs in use are briefly described below:

Rivastigmine is a non-selective pseudoreversible acetylcholinesterase inhibitor that inhibits both butyrylcholinesterase (BuChE) and acetylcholinesterase (unlike donepezil, which selectively inhibits acetylcholinesterase). It is thought to work by inhibiting these cholinesterase enzymes, which would otherwise break down the brain neurotransmitter acetylcholine.

Galantamine is a weak competitive and reversible cholinesterase inhibitor in all areas of the body and also a potent allosteric potentiating ligand of human nicotinic acetylcholine receptors (nAChRs) α4β2, α7/5-HT3, α3β4, and α6β4 in certain areas of the brain. It increases the concentration and thereby action of acetylcholine in certain parts of the brain. It has shown activity in modulating the nicotinic cholinergic receptors on cholinergic neurons to increase acetylcholine release.

Donepezil binds and inactivates reversibly and non-competitively the cholinesterases, thus inhibiting hydrolysis of acetylcholine. It is selective for AChE over BuChE. This results in an increased acetylcholine concentrations at cholinergic synapses. In addition to its actions as an acetylcholinesterase inhibitor, donepezil has been found to act as a potent agonist of the σ1 receptor (Ki=14.6 nM), and has been shown to produce specific anti-amnestic effects in animals mainly via this action.

Memantine is an NMDA receptor antagonist, which reduces certain types of brain activity by binding to NMDA receptors on brain cells and blocking the activity of the neurotransmitter glutamate. At normal levels, glutamate aids in memory and learning, but if levels are too high, glutamate appears to overstimulate nerve cells, killing them through excitotoxicity.

Memantine is a low-affinity voltage-dependent uncompetitive antagonist at glutamatergic NMDA receptors. By binding to the NMDA receptor with a higher affinity than $Mg^{2+}$ ions, memantine is able to inhibit the prolonged influx of $Ca^{2+}$ ions, particularly from extrasynaptic receptors, which forms the basis of neuronal excitotoxicity.

Memantine acts as a non-competitive antagonist at different neuronal nicotinic acetylcholine receptors (nAChRs) at potencies possibly similar to the NMDA and 5-HT3 receptors, but this is difficult to ascertain with accuracy because of the rapid desensitization of nAChR responses in these experiments. It has also been reported that memantine can increase extracellular acetylcholine in the nucleus accumbens and the ventral tegmental areas (see Shearman, E, Rossi, S, Szasz, B, Juranyi, Z, Fallon, S et al. (2006) Changes in cerebral neurotransmitters and metabolites induced by acute donepezil and memantine administrations: A microdialysis study. *Brain Research Bulletin* 69:204-213).

In embodiments of the invention, it will be appreciated that the compound which directly modifies synaptic neurotransmission in the brain will preferably be one or both of an acetylcholinesterase inhibitor or an NMDA antagonist. It may be any of the AD therapeutics described above, or active analogs or salts of any of these.

FTLD Syndromes

The term frontotemporal lobar degeneration (FTLD) refers to a group of progressive brain diseases in which a mild to severe decrease in overall brain weight and atrophy of the frontal and temporal lobes occur. Thinning of the cortical ribbon and discoloration of white matter may also be present. In other cases, atrophy may extend into the parietal lobes, amygdala, hippocampus, thalamus and basal ganglia (head of the caudate nucleus). Ventricular enlargement is also be observed, as well as pallor of the substantia nigra, atrophy of the anterior nerve roots and discoloration of the lateral funiculus in the spinal cord.

Much of the gross atrophy seen at pathology results from synapse loss, dendritic atrophy and neuron loss often accentuated in superficial layers.

Remaining neurons show two distinctive histologic features: swelling (called "ballooned" or "Pick cell") and an inclusion within the perikaryon, most often in layer II (Pick body). Pick bodies are usually found in limbic (greatest concentration is in the amygdala and hippocampus, including the dentate gyrus), paralimbic, and ventral temporal lobe cortex, but may also be seen in anterior frontal and dorsal temporal lobes. They are rarely found elsewhere in the brain. Pick bodies are composed of randomly arranged filaments of the tau protein.

Depending on the primary site of atrophy, the clinical manifestation is dominated by behavior alterations or impairment of language. The onset of symptoms usually occurs before the age of 60 years, and the mean survival from diagnosis varies between 3 and 10 years. The prevalence is estimated at 15 per 100,000 in the population aged between 45 and 65 years. There are two major clinical subtypes, behavioral-variant frontotemporal dementia and primary progressive aphasia. A third subtype is semantic dementia (Riedl, L, Mackenzie, IR, Forstl, H, Kurz, A, Diehl-Schmid, J (2014) Frontotemporal lobar degeneration: current perspectives. Neuropsychiatric Disease and Treatment 10:297-3).

The core clinical diagnostic features for the most common FTLD syndromes are shown in the Table below:

Clinical Profile and Core Diagnostic Features of FTLD Syndromes

| FTLD Syndrome -Clinical Profile | Core Diagnostic Features |
|---|---|
| Frontotemporal Dementia<br>Character change and disordered social conduct are the dominant features initially and throughout the disease course. Instrumental functions of perception, spatial skills, praxis and memory are intact or relatively well preserved. | 1. Insidious onset and gradual progression<br>2. Early decline in social interpersonal conduct<br>3. Early impairment in regulation of personal conduct<br>4. Early emotional blunting<br>5. Early loss of insight |
| Semantic Dementia<br>Semantic disorder (impaired understanding of word meaning and/or object identity) is the dominant feature initially and throughout the disease course. Other aspects of cognition, including autobiographic memory, are intact or relatively well preserved. | A) Insdious onset and gradual progression<br>B) Language disorder characterised by<br>  1. Progressive, fluent empty speech<br>  2. Loss of word meaning manifest by impaired naming and comprehension<br>  3. Semantic paraphasias and/or<br>  4. Perceptual disorder characterised by<br>  1. Prosopagnosia: impaired recognition of identity of familiar faces and/or<br>  2. Associative agnosia: impaired recognition of object identity<br>C) Preserved perceptual matching and drawing reproduction<br>D) Preserved single word repetition<br>E) Preserved ability to read aloud and write to dictation orthographically regular words |
| Progressive Non-fluent Aphasia<br>Disorder of expressive language is the dominant feature initially and throughout the disease course. Other aspects of cognition are intact or relatively well preserved. | A) Insidious onset and gradual progression<br>B) Non-fluent spontaneous speech with at least one of the following: agrammatism, phonemic paraphasias or anomia |

About 10-20 percent of people with FTD disease will also develop a concomitant/overlapping disorder such as a motor disorder, either before or after the start of dementia. The motor disorders most likely associated with FTD are: motor neurone disease [amyotrophic lateral sclerosis, ALS]; progressive supranuclear palsy; corticobasal degeneration. Argyrophilic grain disease is another disorder which sometimes presents with FTD disease.

Because of this association, these indications are also considered "FTLD syndromes".

MT Compounds and Their Use in the Invention

About 40% or more of FTLD patients have FTLD with tau pathology (FTLD-tau), about 50% have TDP-43 (TAR DNA-binding protein 43) pathology (FTLD-TDP), and the remaining 10% have inclusions positive for fused in sarcoma (FUS; FTLD-FUS) or ubiquitin/p62 (FTLD-UPS [ubiquitin proteasome system])

As explained hereinbefore, MT has a mode of action which targets and can reduce both tau and TDP-43 protein aggregation in cells, which is a pathological feature of the disorders described above.

In addition laboratory data shows that methylthioninium inhibits the formation of TDP-43 aggregates in SH-SYSY cells. Following treatment of cells with 0.05 μM MT, the number of intracellular TDP-43 aggregates was reduced by 50%. These findings were confirmed by immunoblot analysis (Yamashita et al 2009).

Example MT compounds useful in the practice of the present invention will now be described in more detail.

Methylthioninium Moiety

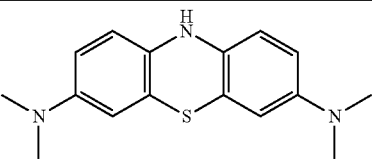

| | | |
|---|---|---|
| Structure | | |
| IUPAC | N3,N3,N7,N7-tetramethyl-10H-phenothiazine-3,7-diamine | N3,N3,N7,N7-tetramethylphenothiazin-5-ium-3,7-diamine |
| Composition | Formula Weight: 285.41 (1)<br>Exact Mass: 285.1299683 (1)<br>Formula: $C_{16}H_{19}N_3S$<br>Composition: C 67.33% H 6.71% N 14.72% S 11.23% | Formula Weight: 284.40 (1)<br>Exact Mass: 284.1215947 (1)<br>Formula: $C_{16}H_{18}N_3S$<br>Composition: C 67.57% H 6.38% N 14.78% S 11.27% |
| Synonym | leucomethylthioninium (LMT) | oxidized methylthioninium ($MT^+$) |

The MT-containing compounds used in the present invention can contain MT in either reduced or oxidised form.

Specifically, the compounds may comprise either of the MT moieties described above. The MT moieties per se described above are not stable. They will therefore be administered as MT compounds—for example LMT or MT⁺ salts.

MT⁺ salts will generally include one or more anionic counter ions (X⁻) to achieve electrical neutrality. The compounds may be hydrates, solvates, or mixed salts of the MT⁺ salt.

LMT containing compounds will generally be stabilised, for example by the presence of one or more protic acids e.g. two protic acids.

The MT content of such salts can be readily calculated by those skilled in the art based on the molecular weight of the compound, and the molecular weight of the MT moiety. Examples of such calculations are given herein.

LMT Compounds

Preferably the MT compound is an LMT compound.

Preferably the MT compound is an "LMTX" compound of the type described in WO2007/110627 or WO2012/107706.

Thus the compound may be selected from compounds of the following formula, or hydrates or solvates thereof:

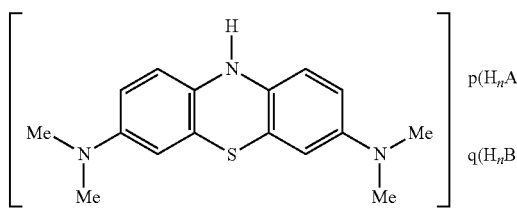

Options:
p = 1, 2
q = 0, 1
n = 1, 2
(p + q) x n = 2

Each of $H_nA$ and $H_nB$ (where present) are protic acids which may be the same or different.

By "protic acid" is meant a proton (H⁺) donor in aqueous solution. Within the protic acid $A^-$ or $B^-$ is therefore a conjugate base. Protic acids therefore have a pH of less than 7 in water (that is the concentration of hydronium ions is greater than $10^{-7}$ moles per litre).

In one embodiment the salt is a mixed salt that has the following formula, where HA and HB are different monoprotic acids:

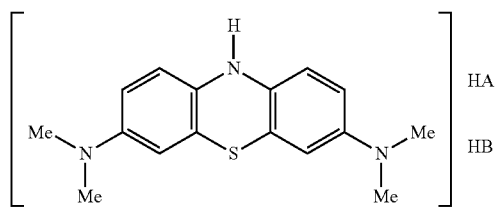

when:
p = 1
q = 1
n = 1
(1 + 1) x 1 = 2

However preferably the salt is not a mixed salt, and has the following formula:

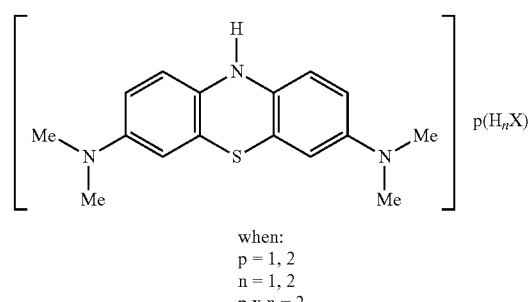

when:
p = 1, 2
n = 1, 2
p x n = 2 wherein each of HnX is a protic acid, such as a di-protic acid or mono-protic acid.

In one embodiment the salt has the following formula, where $H_2A$ is a di-protic acid:

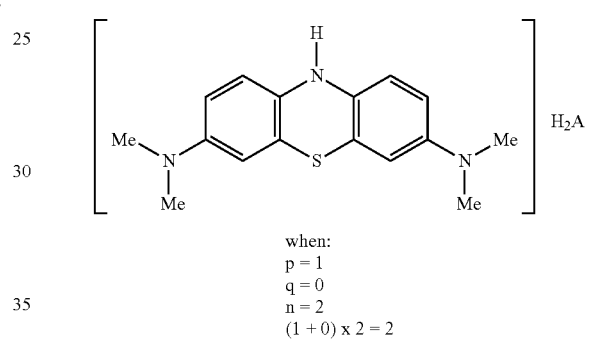

when:
p = 1
q = 0
n = 2
(1 + 0) x 2 = 2

Preferably the salt has the following formula which is a bis monoprotic acid:

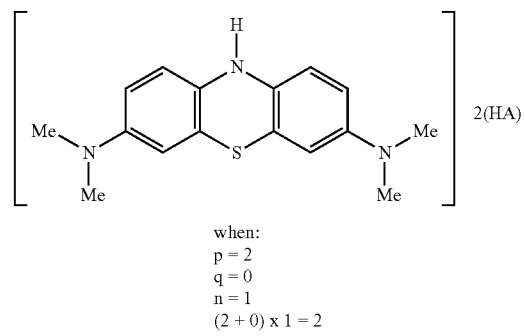

when:
p = 2
q = 0
n = 1
(2 + 0) x 1 = 2

Examples of protic acids which may be present in the LMTX compounds used herein include:

Inorganic acids: hydrohalide acids (e.g., HCl, HBr), nitric acid ($HNO_3$), sulphuric acid ($H_2SO_4$)

Organic acids: carbonic acid ($H_2CO_3$), acetic acid ($CH_3COOH$), methanesulfonic acid, 1,2-Ethanedisulfonic acid, ethansulfonic acid, Naphthalenedisulfonic acid, p-toluenesulfonic acid, Preferred acids are monoprotic acid, and the salt is a bis(monoprotic acid) salt.

A preferred MT compound is LMTM:

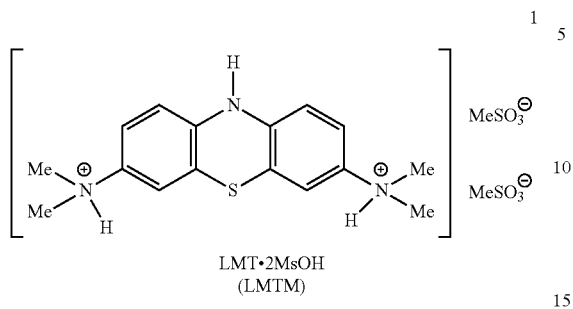

LMT·2MsOH
(LMTM)

Other example LMTX compounds are as follows:

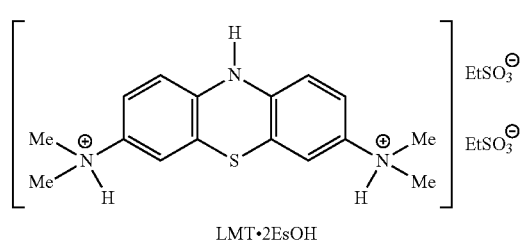

LMT·2EsOH

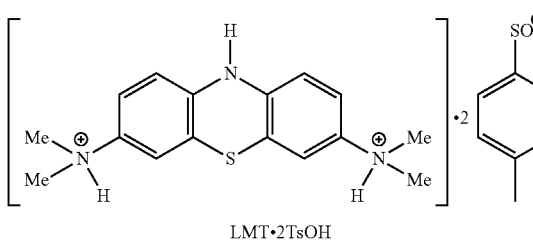

LMT·2TsOH

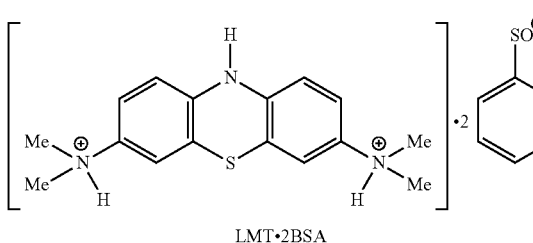

LMT·2BSA

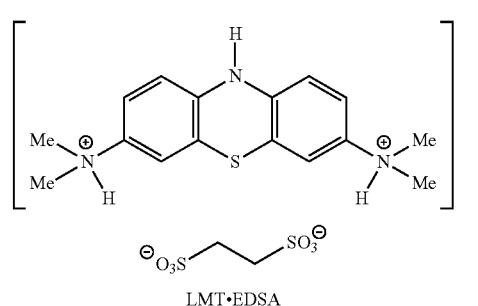

LMT·EDSA

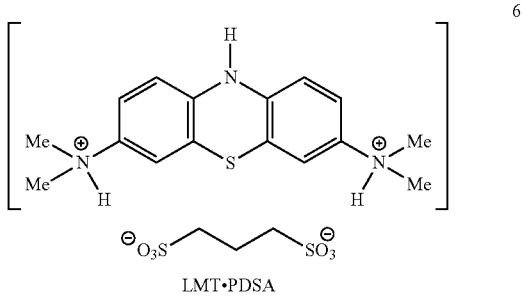

LMT·PDSA

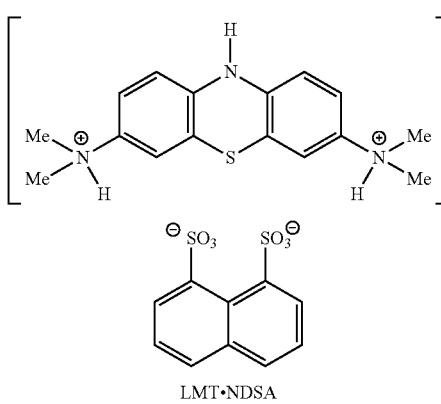

LMT·NDSA

LMT·2HCl

Oxidised MT Compounds

In another embodiment the MT compound is an $MT^+$ compound.

Preferably the MT compound is an $MT^+$ compound of the type described in WO96/30766 or WO2007/110630.

Thus the compound may be selected from compounds of the following formula, or hydrates, solvates, or mixed salts thereof:

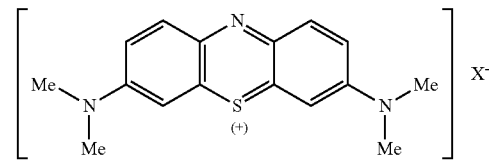

Where $X^-$ is an anionic counter ion.

In some embodiments of the present invention the $MT^+$ compound is MTC, for example a "high purity" MTC as described below.

In some embodiments of the present invention the $MT^+$ compound is not MTC.

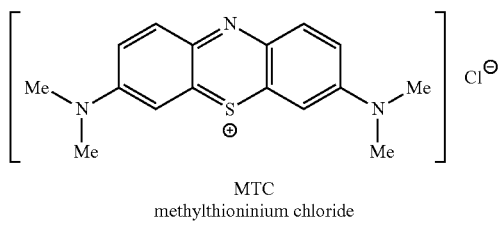

MTC
methylthioninium chloride

As explained in WO2011/036561 and WO2011/036558, MTC occurs in a number of polymorphic forms having different levels of hydration.

A preferred MTC polymorph for use in the methods and compositions described herein is 'form A' described in WO2011/036561 which is a pentahydrate, at a "high purity" described above. That has a molecular weight of around 409.9.

In some embodiments of the present invention, the MT$^+$ compound is a high purity MTC. In this context 'high purity' is defined by one or more of the criteria set out below.

In some embodiments, the MTC has a purity of greater than 97%.

In some embodiments, the MTC has a purity of greater than 98%.

In some embodiments, the MTC has a purity of greater than 99%.

In some embodiments, the MTC has less than 2% Azure B as impurity.

In some embodiments, the MTC has less than 1% Azure B as impurity.

In some embodiments, the MTC has less than 0.5% Azure B as impurity.

In some embodiments, the MTC has less than 0.1% Azure B as impurity.

In some embodiments, the MTC has less than 0.15% Azure A as impurity.

In some embodiments, the MTC has less than 0.10% Azure A as impurity.

In some embodiments, the MTC has less than 0.05% Azure A as impurity.

In some embodiments, the MTC has less than 0.15% Azure C as impurity.

In some embodiments, the MTC has less than 0.10% Azure C as impurity.

In some embodiments, the MTC has less than 0.05% Azure C as impurity.

In some embodiments, the MTC has less than 0.13% MVB (Methylene Violet Bernstein) as impurity.

In some embodiments, the MTC has less than 0.05% MVB as impurity.

In some embodiments, the MTC has less than 0.02% MVB as impurity.

All percentage purities recited herein are by weight unless otherwise specified.

In some embodiments, the MTC has an elementals purity that is better than that specified by the European Pharmacopeia (EP).

As used herein, the term 'elementals purity' pertains to the amounts of the twelve (12) metals specified by the European Pharmacopeia: Al, Cd, Cr, Cu, Sn, Fe, Mn, Hg, Mo, Ni, Pb, and Zn. The current edition of the European Pharmacopeia (8th Edition, supplementum 8.8) specifies the following limits for these metals:

| European Pharmacopeia 8.8 (EP8.8) | |
|---|---|
| Element | Maximum content (µg/g) |
| Aluminium (Al) | 100 |
| Cadmium (Cd) | 1 |
| Chromium (Cr) | 100 |
| Copper (Cu) | 300 |
| Tin (Sn) | 10 |
| Iron (Fe) | 200 |
| Manganese (Mn) | 10 |
| Mercury (Hg) | 1 |
| Molybdenum (Mo) | 10 |
| Nickel (Ni) | 10 |
| Lead (Pb) | 10 |
| Zinc (Zn) | 100 |

In one embodiment, the MTC has an elementals purity (e.g. for each of Al, Cd, Cr, Cu, Sn, Fe, Mn, Hg, Mo, Ni, Pb, and Zn) which is equal to or better than (i.e. lower than) the EP8.8 values set out in the table above.

In one embodiment, the MTC has an elementals purity which is equal to or better than 0.9 times the EP8.8 values set out in the table above.

In one embodiment, the MTC has an elementals purity which is equal to or better than 0.8 times the EP8.8 values set out in the table above.

In one embodiment, the MTC has an elementals purity which is equal to or better than 0.7 times the EP8.8 values set out in the table above.

In one embodiment, the MTC has an elementals purity which is equal to or better than 0.5 times the EP8.8 values set out in the table above.

(For example, 0.5 times the EP8.8 values as set out above are 50 µg/g Al, 0.5 µg/g Cd, 50 µg/g Cr, etc.)

In one embodiment the MTC has a chromium level that is equal to or better than (i.e. lower than) 100 µg/g.

In one embodiment the MTC has a chromium level that is equal to or better than (i.e. lower than) 10 µg/g.

In one embodiment the MTC has a copper level that is equal to or better than (i.e. lower than) 300 µg/g.

In one embodiment the MTC has a copper level that is equal to or better than (i.e. lower than) 100 µg/g.

In one embodiment the MTC has a copper level that is equal to or better than (i.e. lower than) 10 µg/g.

In one embodiment the MTC has an iron level that is equal to or better than (i.e. lower than) 200 µg/g.

In one embodiment the MTC has an iron level that is equal to or better than (i.e. lower than) 100 µg/g.

All plausible and compatible combinations of the above purity grades are disclosed herein as if each individual combination was specifically and explicitly recited.

In particular embodiments, the MTC is a high purity MTC wherein 'high purity' is characterised by a purity of greater than 98% and one or more of the following:
  (i) less than 2% Azure B as impurity;
  (ii) less than 0.13% MVB (Methylene Violet Bernstein) as impurity; or
  (iii) an elementals purity better than the European Pharmacopeia limits of less than 100 µg/g Aluminium (Al); less than 1 µg/g Cadmium (Cd); less than 100 µg/g Chromium (Cr);
  less than 300 µg/g Copper (Cu); less than 10 µg/g Tin (Sn); less than 200 µg/g Iron (Fe);

less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

In particular embodiments, the MTC is a high purity MTC wherein high-purity is characterised by a purity of greater than 98% and one or more of the following:
  (i) less than 1% Azure B as impurity;
  (ii) less than 0.15% Azure A as impurity;
  (iii) less than 0.15% Azure C as impurity;
  (iv) less than 0.13% Methylene Violet Bernthsen (MVB) as impurity;
  (v) an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

In particular embodiments, the MTC is a high purity MTC wherein high-purity is characterised by a purity of greater than 98% and one or more of the following:
  (i) less than 1% Azure B as impurity;
  (ii) less than 0.15% Azure A as impurity;
  (iii) less than 0.15% Azure C as impurity;
  (iv) less than 0.05% Methylene Violet Bernthsen (MVB) as impurity; or
  (v) an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

In particular embodiments, the MTC is a high purity MTC wherein high-purity is characterised by at least 98% purity and less than 1% Azure B as impurity.

In particular embodiments, the MTC is a high purity MTC wherein high-purity is characterised by:
  (i) at least 98% purity
  (i) less than 1% Azure B as impurity; and
  (ii) an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

In particular embodiments, the MTC is a high purity MTC wherein high-purity is characterised by at least 98% purity and an elementals purity better than the European Pharmacopeia limits of less than 100 µg/g Aluminium (Al); less than 1 µg/g Cadmium (Cd); less than 100 µg/g Chromium (Cr); less than 300 µg/g Copper (Cu); less than 10 µg/g Tin (Sn); less than 200 µg/g Iron (Fe); less than 10 µg/g Manganese (Mn); less than 1 µg/g Mercury (Hg); less than 10 µg/g Molybdenum (Mo); less than 10 µg/g Nickel (Ni); less than 10 µg/g Lead (Pb); and less than 100 µg/g Zinc (Zn).

Methods for the production of 'high purity' diaminophenothiazinium compounds, including MTC, are described, for example, in WO2006/032879 and WO2008/007074 (WisTa Laboratories Ltd) and in WO2008/006979 (Provence Technologies).

Other example MT compounds are described in WO2007/110630. Their molecular weight (anhydrous) is also shown:

|    | Compound       | Molecular weight |
|----|----------------|------------------|
| 10 | MTC. 0.5ZnCl$_2$ | 388.0            |
| 11 | MTI            | 411.3            |
| 12 | MTI.HI         | 539.2            |
| 13 | MT.NO$_3$      | 346.4            |

The dosages described herein with respect to MT thus apply mutatis mutandis for these MT containing compounds, as adjusted for their molecular weight, and for choice of hydrate if used. For example MTC.0.5ZnCl$_2$ (also referred to as 'METHYLENE BLUE ZINC CHLORIDE DOUBLE SALT; Cl 52015) may be obtained commercially as a monohydrate by several suppliers, which would have a molecular weight higher by 18. MTI is reportedly available as a hemihydrate, In the various aspects of the invention described herein (as they relate to an MT-containing compound) this may optionally be any of those compounds described above:
  In one embodiment, it is compound 1.
  In one embodiment, it is compound 2.
  In one embodiment, it is compound 3.
  In one embodiment, it is compound 4.
  In one embodiment, it is compound 5.
  In one embodiment, it is compound 6.
  In one embodiment, it is compound 7.
  In one embodiment, it is compound 8.
  In one embodiment, it is compound 9.
  In one embodiment, it is compound 10.
  In one embodiment, it is compound 11.
  In one embodiment, it is compound 12.
  In one embodiment, it is compound 13.

Or the compounds may be a hydrate, solvate, or mixed salt of any of these.

Example Dosages of MT Compounds

Dosages described hereinafter are premised on the basis that the patient is an adult human (typical weight 50 to 70 kg). If desired, corresponding dosages may be utilised for subjects outside of this range by using a subject weight factor whereby the subject weight is divided by 60 kg to provide the multiplicative factor for that individual subject.

Dosages described herein are based on amounts of "MT" core. Corresponding dosages of MT-containing compounds can be readily provided using "the weight factors" based on a molecular weight of 285 for the LMT core (or 284 for the MT$^+$ core).

By "weight factor" is meant the relative weight of the pure MT containing compound vs. the weight of MT which it contains. For example the weight factor for LMTM is 1.67. Other weight factors can be calculated for the example MT compounds herein, and the corresponding dosage ranges can be calculated therefrom.

In the practice of the present invention, the MT administration will typically provide a total of between 0.5 and 400 mg of MT to the subject per day, optionally split into 2 or more doses.

An example dosage is 1 to 350 mg.
A further example dosage is 2 to 300 mg.
A further example dosage is 4 to 250 mg.
A further preferred dosage is 6 to 240 mg.
A further preferred dosage is 7 to 220 mg.

As explained herein, the results of the phase 3 clinical trial indicate that even a relatively low dose of the MT compound (4 mg LMTM b.id., 8 mg LMTM total per day) which was used in the trial as a control) may show benefit in FTD, as compared to the cognitive decline seen in historical controls. This is independent of whether an AD treatment was given as an add-on treatment.

Therefore in one other aspect of the present embodiment there is provided a method of treatment (therapeutic or prophylactic) of an FTLD syndrome in a subject, which method comprises administering to said subject a methylthioninium (MT)-containing compound, said administration of MT compound providing a total of between 0.5 and 20 mg of MT to the subject per day, optionally split into 2 or more doses. Optionally the MT compound is provided in combination with a treatment which modifies synaptic neurotransmission in the brain.

The total MT dose may be from around any of 0.5, 1, 1.5, 2, 2.5, 3, 3.5, 4 mg to around any of 5, 6, 7, 8, 9, 10, 11, 12, 13, 14, 15, 16, 17, 18, 19, 20 mg.

An example MT dosage is 1 to 20 mg.
A further example MT dosage is 2 to 15 mg.
A further example MT dosage is 3 to 10 mg.
A further preferred MT dosage is 3.5 to 7 mg.
A further preferred MT dosage is 4 to 6 mg.

Adsorption Factors

The findings that unexpectedly low doses of MT salts showed therapeutic benefits in treating FTLD syndromes was demonstrated using an example LMTX salt. However this finding has implications for the dosing of both LMT and MT$^+$ salts.

The present inventors have determined that dosing with LMTX salts permits more efficient adsorption, compared with MT$^+$ salts. Typically MT adsorption may be around 1.5× greater when delivered as an LMTX salt as opposed to an MT$^+$ salts. This 1.5 factor may be termed herein an "adsorption factor".

Therefore in certain embodiments of the invention, the dosed amount of MT$^+$ salt may be higher than when using LMTX salt to achieve a similar plasma concentration.

Thus one preferred dosage of MT$^+$ salt may be about 5.25 to 10.5 mg MT, which is expected to provide a similar adsorbed dosage as 3.5 to 7 mg MT when delivered as LMTX.

Any of the MT compounds described herein, may be formulated with a reducing agent. In particular, MT$^+$ salts such as MTC may be formulated with a reducing agent such as ascorbate, and then lyophilized (as described in WO02/055720). This is expected to improve adsorption of the MT delivered by the compound.

Accumulation Factors

As will be appreciated by those skilled in the art, for a given daily dosage, more frequent dosing will lead to greater accumulation of a drug.

The present inventors have derived estimated accumulation factors for MT as follows:

| Dosing | Observed plasma accumulation for MT | Relative accumulation |
|---|---|---|
| Once daily | 1.29$^{extrapolated}$ | 1 |
| Twice daily | 1.47 | 1.13 |
| Three-times daily | 1.65 | 1.28 |

As explained below, when administering MT in the reduced (LMT) form, it may be desired to use a smaller total amount within the recited range, compared to the oxidised (MT$^+$) form.

As explained below, when administering the MT dose split in a larger number of doses/day it may be desired to use a smaller total amount within the recited range, compared to a single daily dosing, or a smaller number of doses per day.

Dosages of Neurotransmission Modifying Compounds

The dosage of the neurotransmission modifying compound used in the combination FTD treatments will generally be consistent with that normally given when the same compound is administered for treatment of AD although lower or higher dosages may be used consistent with safety limits of the drug in question. Some typical dosages for common treatments are summarised as follows. However it will be appreciated that other dosages may be also be appropriate e.g. for atypical formulations or modes of administration (e.g. extended release formulations or 'patch' versions).

Donepezil: A dose of 10 mg once a day is typically administered after patients have been on a daily dose of 5 mg for at least 4 to 6 weeks. A dose of 23 mg once a day can be administered after patients have been on a dose of 10 mg once daily for at least 3 months.

Rivastigmine: The recommended dosage of Rivastigmine tartrate capsules in AD is 6 mg to 12 mg per day, split twice a day (daily doses of 3 mg to 6 mg twice a day). An initial dose may therefore be, for example, 4 mg orally twice a day, preferably with morning and evening meals.

Galantamine: After a minimum of four weeks of treatment, if the initial dosage is well tolerated, a maintenance dose of 8 mg twice a day may be used. A further increase to 12 mg twice a day should be attempted only after a minimum of 4 weeks at the previous dosage. The maximum dose is 16 to 24 mg/day.

Memantine: Initial dose: 5 mg orally once a day, then titrated upwards by 5 mg per week. Maintenance dose: 5 mg once a day up to 10 mg twice a day. Maximum dose: 20 mg per day.

Duration and Effect of Treatment

For treatment of the FLTD syndrome described herein, a treatment regimen based will preferably extend over a sustained period of time. The particular duration would be at the discretion of the physician.

For example, the duration of treatment may be:
At least 1, 2, 3, 4, 5, 6, 7, 8, 9, 10, 11, 12 months, or longer.
At least 2, 3, 4, 5 years, or longer.
Between 6 and 12 months.
Between 1 and 5 years.

In preferred embodiments the duration may be such as to achieve a arrest or 'reduction in decline' of one or more criteria used to assess severity of FTLD syndromes. For example a minimum reduction in decline over the course of one year may be at least equal to the following values:

| Scale | (a) Preferred reduction in decline | (b) More preferred reduction in decline | (c) Most preferred reduction in decline |
|---|---|---|---|
| ACE-R (points) | 3 | 8 | 12 |
| FAQ (points) | 1 | 2 | 5 |
| FRTM (cm$^3$) | 0.2 | 0.5 | 1.5 |
| MMSE (points) | 1 | 2 | 4 |

This may be assessed by comparison with suitable control or control subjects receiving the same regimen using a placebo. Thus, for example, where a control FTLD population shows a decline in ACE-R of 15 points (−15) over a specified time such as 1 year; a preferred 3 point reduction in decline would show as a −12 decline over that period.

In other embodiments the treatment may be sufficient to arrest decline, or indeed show some cognitive benefit, For prophylaxis, the treatment may be ongoing.

In all cases the treatment duration will generally be subject to advice and review of the physician.

Oral Dosage Forms

The active ingredient compounds described herein (MT and\or AD treatments) may be used in the aspects and embodiments of the invention in the form of pharmaceutical compositions comprising the compound. Preferably there are administered to a subject/patient orally.

Thus in one aspect there is provided a pharmaceutical composition comprising (as active ingredients):

(i) a first compound which is a methylthioninium (MT) compound in combination; and (ii) a second compound, which second compound directly modifies synaptic neurotransmission in the brain.

The pharmaceutical composition may be adapted to treat FTLD syndromes as described herein.

The MT-compound and the compound directly modifies synaptic neurotransmission in the brain are preferably selected from the examples given herein e.g. by way of non-limiting example, an LMT compound in combination with an acetylcholinesterase inhibitor.

Preliminary experiments by the present inventors have shown these types of compound are physically compatible.

The compositions may be characterised in that they are unitary compositions for oral administration to a human, for example in the form of ingestible tablets, buccal tablets, troches capsules, elixirs, suspensions etc. as described in more detail below.

The compounds may be present in the pharmaceutical composition in therapeutically or prophylactically effective amounts, in accordance with the example dosages and desired effects described herein.

For example the compound directly modifies synaptic neurotransmission in the brain may be present as follows:

Donepezil: between 5 and 23 mg e.g. 5, 10, 15, 20, 23 mg.

Rivastigmine: between 3 and 12 mg e.g. 3, 4, 5, 6, 8, 10 12 mg.

Galantamine: between 4 and 24 mg e.g. 4, 8, 12, 16, 20, 24 mg.

Memantine: between 5 and 20 mg e.g. 5, 10, 15, 20 mg.

For example the MT may be present as follows:

An example dosage unit may contain 0.5 to 60 mg.

A further example dosage unit may contain 0.5 to 10 mg.

A further example dosage unit may contain 1 to 10 mg of MT.

A further example dosage unit may contain 2 to 9 mg of MT.

A further example dosage unit may contain 3 to 8 mg of MT.

A further preferred dosage unit may contain 3.5 to 7 mg of MT.

A further preferred dosage unit may contain 4 to 6 mg of MT.

In some embodiments, the amount is about 1, 1.5, 2, 2.5, 3, 3.5, 4, 5, 6, 7, 8, 9, 10 mg of MT.

As explained above, the MT weight factor for LMTM is 1.67. Since it is convenient to use unitary or simple fractional amounts of active ingredients, non-limiting example LMTM dosage units may include 1.5, 2, 2.5, 3, 3.5, 4, 5, 6, 7, 8, 9, 10, 15, 16, 17, 18, 19, 20, 30, 40, 50, 60, 70, 80, 90, 100 mg etc.

As explained above, the MT weight factor for $MTC.5H_2O$ is 1.44. Since it is convenient to use unitary or simple fractional amounts of active ingredients, non-limiting example $MTC.5H_2O$ dosage units may include 1.5, 2, 2.5, 3, 3.5, 4, 5, 6, 7, 8, 9, 10, 15, 18, 20, 40, 50, 60, 70, 80 mg etc.

Where the composition is to be taken twice daily, any of these amounts may be reduced by a factor of 2.

Non-limiting examples include 4 mg LMTM plus 10 or 20 mg Donezipil.

Non-limiting examples include 4 mg LMTM plus 6 or 12 mg Rivastigmine.

Non-limiting examples include 4 mg LMTM plus 5, 10, or 20 mg Memantine.

Non-limiting examples include 10 mg LMTM plus 10 or 20 mg Donezipil.

Non-limiting examples include 10 mg LMTM plus 6 or 12 mg Rivastigmine.

Non-limiting examples include 10 mg LMTM plus 5, 10, or 20 mg Memantine.

Non-limiting examples include 30 mg LMTM plus 10 or 20 mg Donezipil.

Non-limiting examples include 30 mg LMTM plus 6 or 12 mg Rivastigmine.

Non-limiting examples include 30 mg LMTM plus 5, 10, or 20 mg Memantine.

Non-limiting examples include 50 mg LMTM plus 10 or 20 mg Donezipil.

Non-limiting examples include 50 mg LMTM plus 6 or 12 mg Rivastigmine.

Non-limiting examples include 50 mg LMTM plus 5, 10, or 20 mg Memantine.

Generally, the pharmaceutical compositions of the invention (e.g., formulation, preparation, medicament) will comprising a compound or compounds as described herein, and a pharmaceutically acceptable carrier, diluent, or excipient.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

In some embodiments, the composition is a pharmaceutical composition comprising the compound(s), as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In some embodiments, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, N.Y., USA), Remington's Pharmaceutical Sciences, 20th edition, pub. Lippincott, Williams & Wilkins, 2000; and Handbook of Pharmaceutical Excipients, 2nd edition, 1994.

In some embodiments, the dosage unit is a tablet.

In some embodiments, the dosage unit is a capsule.

In some embodiments, said capsules are gelatine capsules.

In some embodiments, said capsules are HPMC (hydroxypropylmethylcellulose) capsules.

The formulations may be prepared by any methods well known in the art of pharmacy. Such methods include the step of bringing into association the compound(s) with a carrier which constitutes one or more accessory ingredients. In general, the formulations are prepared by uniformly and intimately bringing into association the compound(s) with carriers (e.g., liquid carriers, finely divided solid carrier, etc.), and then shaping the product, if necessary.

In some embodiments, the pharmaceutically acceptable carrier, diluent, or excipient is or comprises one or both of a glyceride (e.g., Gelucire 44/14 ®; lauroyl macrogol-32 glycerides PhEur, USP) and colloidal silicon dioxide (e.g., 2% Aerosil 200®; Colliodal Silicon Dioxide PhEur, USP).

Preferably the pharmaceutical compositions comprising compound(s) of the invention, in solid dosage form. The composition preferably further comprises at least one diluent suitable for dry compression. The pharmaceutical composition is characterised in that the compound(s) exist in a substantially stable form.

The pharmaceutical composition will generally also include a lubricant. Examples of lubricants include magnesium stearate, calcium stearate, sodium stearyl fumarate, stearic acid, glycerylbehaptate, polyethylene glycol, ethylene oxide polymers (for example, those available under the registered trademark Carbowax from Union Carbide, Inc., Danbury, Conn.), sodium lauryl sulphate, magnesium lauryl stearate, mixtures of magnesium stearate with sodium lauryl sulphate, and hydrogenated vegetable oil. Preferred lubricants include calcium stearate, magnesium stearate and sodium stearyl fumarate. Most preferred as the lubricant is magnesium stearate. Lubricants generally comprise from about 0.5 to about 5.0% of the total (uncoated) tablet weight. The amount of lubricant employed is generally from about 1.0 to about 2.0%, preferably 0.5 to 2.0% w/w.

In addition to the diluent(s) and lubricant(s), other conventional excipients may also be present in the pharmaceutical compositions of the invention. Such additional excipients include disintegrants, binders, flavouring agents, colours and glidants. Some excipients can serve multiple functions, for example as both binder and tablet disintegrant.

A tablet disintegrant may be present in an amount necessary to achieve rapid dissolution. Disintegrants are excipients which oppose the physical forces of particle bonding in a tablet or capsule when the dosage form is placed in an aqueous environment. Examples of disintegrants include crosslinked polyvinylpyrrolidone (crospovidone), sodium starch glycolate, crosslinked sodium carboxymethyl cellulose (sodium croscarmellose), and pregelatinized starch. Generally the amount of disintegrant can be from 0 to about 25% w/w, more commonly from about 1% to about 15% w/w, and usually less than 10% or less than 5% w/w, of the composition.

Binders are excipients which contribute to particle adhesion in a solid formulation. Examples of binders include cellulose derivatives (carboxymethylcellulose, hydroxypropyl methylcellulose, hydroxypropyl cellulose, hydroxyethylcellulose, ethylcellulose, microcrystalline cellulose) and sugars such as lactose, sucrose, dextrose, glucose, maltodextrin, and mannitol, xylitol, polymethacrylates, polyvinylpyrrolidone, sorbitol, pregelatinized starch, alginic acids, and salts thereof such as sodium alginate, magnesium aluminum silicate, polyethylene glycol, carrageenan and the like. Generally, the amount of binder can vary widely, eg from 0% to 95% w/w of the composition. As noted above, excipients may serve multiple functions. For instance, the tabletting diluent may also serve as a binder.

Glidants are substances added to a powder to improve its flowability. Examples of glidants include magnesium stearate, colloidal silicon dioxide (such as the grades sold as Aerosil), starch and talc. Glidants may be present in the pharmaceutical composition at a level of from 0 to about 5% w/w. Again, however, it should be noted that excipients may serve multiple functions. The lubricant, for example magnesium stearate, may also function as a glidant.

Examples of colours that may be incorporated into the pharmaceutical compositions of the invention include titanium dioxide and/or dyes suitable for food such as those known as FD&C dyes and natural colouring agents. A colouring agent is unlikely to be used in the powder mixture that is compressed in accordance with the aspects of the invention discussed above, but may form part of a coating applied to the composition, as described below, in which case the colouring agent may be present in the film coat in an amount up to about 2.0% w/w.

The tablet is desirably coated with a conventional film coating which imparts toughness, ease of swallowing, and an elegant appearance to the final product. Many polymeric film-coating materials are known in the art. A preferred film-coating material is hydroxypropylmethylcellulose (HPMC) or polyvinyl alcohol-part hydrolysed (PVA). HPMC and PVA may be obtained commercially, for example from Colorcon, in coating formulations containing excipients which serve as coating aids, under the registered trademark Opadry. Opadry formulations may also contain talc, polydextrose, triacetin, polyethyleneglycol, polysorbate 80, titanium dioxide, and one or more dyes or lakes. Other suitable film-forming polymers may also be used, including hydroxypropylcellulose, vinyl copolymers such as polyvinyl pyrollidone and polyvinyl acetate, and acrylate-methacrylate copolymers. Use of a film coating is beneficial for ease of handling and because a blue coloured uncoated core may stain the inside of the mouth during swallowing. Coating also improves light stability of the dosage form.

Coating of the tablets may conveniently be carried out using a conventional coating pan. In preferred embodiments of the process, the coating pan is pre-heated using heated inlet air until the exhaust temperature reaches 35°-55° C., more preferably 40-50° C. This may typically require application of heated inlet air at an inlet temperature of 45-75° C., preferably 50-65° C., for 10-15 minutes. The tablet cores containing the active ingredient (e.g. LMTM) are then added to the coating pan and the aqueous film coat applied. The spray rate is controlled such that the bed temperature is maintained at 38-48° C., more preferably 42-44° C., until the desired weight gain (coating weight) has been achieved.

The formulation may be prepared to provide for rapid or slow release; immediate, delayed, timed, or sustained release; or a combination thereof.

An immediate release product allows the ingredient or active moiety to dissolve in the gastrointestinal tract, without causing any delay or prolongation of the dissolution or absorption of the drug. Requirements for dissolution testing of immediate release products are set out in the Guidance for Industry (CDER 1997) "Dissolution testing for immediate release solid oral dosage forms", (CDER 1997) "Immediate release solid oral dosage forms—Scale up and Post approval Changes", ICH Guidance Q6A, Specifications: Test Procedures and Acceptance Criteria For New Drug Substances And New Drug Products. The most commonly employed dissolution test methods as described in the USP and European Pharmacopeia (6th edition) are the basket method (USP 1) and the paddle method (USP 2). The described methods are simple, robust, well standardized, and used worldwide. They are flexible enough to allow dissolution testing for a variety of drug products. The following parameters influencing the dissolution behaviour may for example be relevant for selecting the appropriate in vitro dissolution test conditions for an immediate release solid oral product: apparatus, stirring speed, dissolution medium and temperature.

MT Only Compositions

For compositions containing only MT as the active ingredient, in some embodiments, the amount of MT in the unit will be around 0.5 to 10 mg.

An example dosage unit may contain 1 to 10 mg of MT.

A further example dosage unit may contain 2 to 9 mg of MT.

A further example dosage unit may contain 3 to 8 mg of MT.

A further preferred dosage unit may contain 3.5 to 7 mg of MT.

A further preferred dosage unit may contain 4 to 6 mg of MT.

In some embodiments, the amount is about 1, 1.5, 2, 2.5, 3, 3.5, 4, 5, 6, 7, 8, 9, 10 mg of MT.

Using the weight factors described or explained herein, one skilled in the art can select appropriate amounts of an MT containing compound to use in oral formulations.

As explained above, the MT weight factor for LMTM is 1.67. Since it is convenient to use unitary or simple fractional amounts of active ingredients, non-limiting example LMTM dosage units may include 1.5, 2, 2.5, 3, 3.5, 4, 5, 6, 7, 8, 9, 10, 15, 16, 17, 18 mg etc.

As explained above, the MT weight factor for $MTC.5H_2O$ is 1.44. Since it is convenient to use unitary or simple fractional amounts of active ingredients, non-limiting example $MTC.5H_2O$ dosage units may include 1.5, 2, 2.5, 3, 3.5, 4, 5, 6, 7, 8, 9, 10, 15, 18, 20 mg etc.

Kits of Parts

Dosage compositions described herein (e.g. an MT containing compound and\or a compound which directly modifies synaptic neurotransmission in the brain) plus optionally other ingredients, may be provided in a labelled packet along with instructions for their use in the combination treatments described herein In one embodiment, the pack is a bottle, such as are well known in the pharmaceutical art. A typical bottle may be made from pharmacopoeial grade HDPE (High-Density Polyethylene) with a childproof, HDPE pushlock closure and contain silica gel desiccant, which is present in sachets or canisters. The bottle itself may comprise a label, and be packaged in a cardboard container with instructions for us and optionally a further copy of the label.

In one embodiment, the pack or packet is a blister pack (preferably one having aluminium cavity and aluminium foil) which is thus substantially moisture-impervious. In this case the pack may be packaged in a cardboard container with instructions for us and label on the container.

Said label or instructions may provide information regarding the relevant FTLD syndrome for which the medication is intended. Said label or instructions may provide information instructing the user that the compositions therein should be used in a combination treatment described herein Said label or instructions may provide information regarding the maximum permitted daily dosage of the compositions as described herein—for example based on once daily, b.i.d., or t.i.d.

Said label or instructions may provide information regarding the suggested duration of treatment, as described herein.

Mixtures of Oxidised and Reduced MT Compounds

MT compounds for use in the present invention may include mixtures of the oxidised and reduced form.

In particular, the LMT-containing compounds may include oxidised ($MT^+$) compounds as 'impurities' during synthesis, and may also oxidize (e.g., autoxidize) after synthesis to give the corresponding oxidized forms. Thus, it is likely, if not inevitable, that compositions comprising the compounds of the present invention will contain, as an impurity, at least some of the corresponding oxidized compound. For example an "LMT" salt may include 10 to 15% of $MT^+$ salt.

Salts and Solvates

Although the MT containing compounds described herein are themselves salts, they may also be provided in the form of a mixed salt (i.e., the compound of the invention in combination with another salt). Such mixed salts are intended to be encompassed by the term "and pharmaceutically acceptable salts thereof". Unless otherwise specified, a reference to a particular compound also includes salts thereof.

The compounds of the invention may also be provided in the form of a solvate or hydrate. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, a penta-hydrate etc. Unless otherwise specified, any reference to a compound also includes solvate and any hydrate forms thereof.

Naturally, solvates or hydrates of salts of the compounds are also encompassed by the present invention.

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1 shows the study design of the 52 week parallel group randomized controlled clinical trial for treatment of bvFTD with LMTM.

FIG. 2 shows the study disposition. Originally 369 patients were assessed for eligibility. 149 failed screening, with 75% excluded at pre-screen and 25% excluded at screen. This left 220 patients enrolled and randomised.

EXAMPLES

Example 1—Provision & Formulation of MT-Containing Compounds

Methods for the chemical synthesis of the MT-containing compounds described herein are known in the art. For example:

Synthesis of compounds 1 to 7 can be performed according to the methods described in WO2012/107706, or methods analogous to those.

Synthesis of compound 8 can be performed according to the methods described in WO2007/110627, or a method analogous to those.

Synthesis of compound 9 (MTC) is well known in the art. Examples syntheses of highly pure MTC are provided in WO2006/032879 and WO2008/007074.

Synthesis of compounds 10 to 13 can be performed according to the methods described in WO2007/110630, or methods analogous to those.

Example 2—Availability of AD Therapeutics Compounds

The compounds which directly modify synaptic neurotransmission in the brain useful in the present invention are commercially available as acetylcholinesterase inhibitors (AChEIs) or NMDA receptor antagonists.

Examples of AChEIs include tacrine (Cognex™, First Horizon), donepezil (Aricept™, Eisai/Pfizer), rivastigmine (Exelon™, Novartis), and galantamine (Razadyne™, formerly Reminyl™, Ortho-McNeil). Memantine is available as Ebixa™ or Namenda™ e.g. from Forest.

Example 3—Phase 3 Trial of the Tau and TDP-43 Aggregation Inhibitor, Leuco-Methylthioninium-Bis(Hydromethanesulfonate) (LMTM), for Treatment of Behavioural Variant Frontotemporal Dementia (bvFTD)

Behavioural Variant Frontotemporal Dementia (bvFTD).

FTD is the second most common form of young-onset dementia after Alzheimer's disease and comprises about 10-20% of all dementias worldwide. FTD occurs in about three to 15 per 100 000 individuals aged between 55 years and 65 years. The disease has a slow and subtle onset: it is familial in 30-50% of patients and affects men and women almost equally. The main clinical syndromes are the behavioural variant and the language variants (semantic dementia and progressive nonfluent aphasia [PNFA]):

Clinical Syndrome Subtype Prevalence bvFTD 1.47 in 10,000

SD 0.16 in 10,000

PNFA 0.25 in 10,000

The FTLD pathological spectrum shows 36-50% tau (FTLD-Tau) and 50% TDP-43 (FTLD-TDP). Both pathologies are believed to be treatable by LMTM. bvFTD was selected as the target FTD as it provided the greatest feasibility to recruit within an 18-month time-frame.

Figure 1:
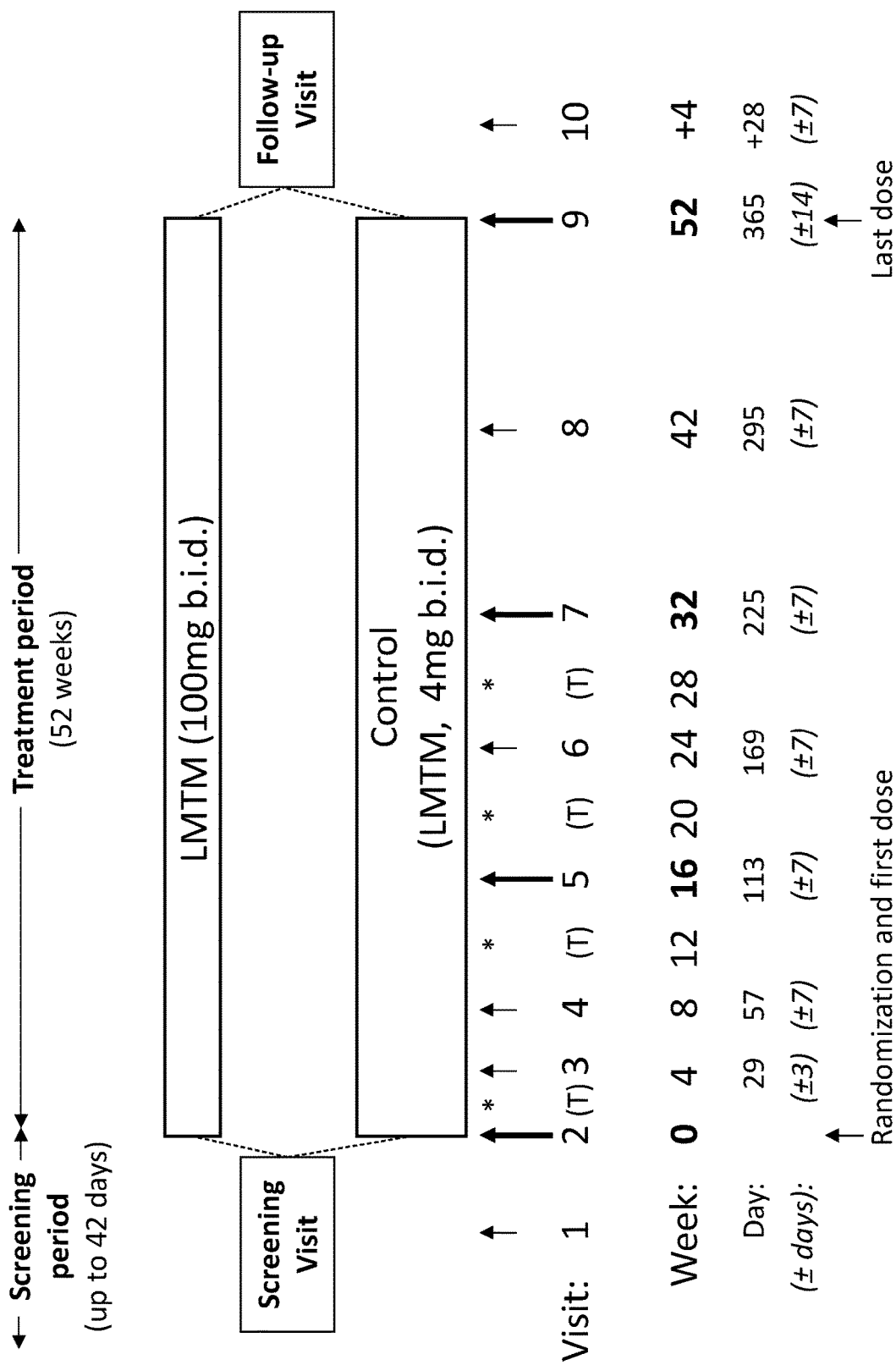

FIG. 1 shows the study design of the 52 Week Parallel Group Randomized Controlled Clinical Trial.

Dose Selection: 4 mg b.i.d. as Control Arm

It is known that LMTM is associated with urine and stool discoloration. To prevent unblinding, 4 mg BID was selected as the control arm, as being the lowest dose to have comparable discoloration in a 14-day and 25-day repeat-dose studies in healthy volunteers.

Dose Selection: Active Treatment Arm

An active dose of LMTM 100 mg BID (200 mg/day) was selected, guided by experience in a phase 2 trial for treatment of mild/moderate AD using MTC (see WO2009/044127).

Example 4—Trial Endpoints

The following endpoints for defined for the phase 3 trial:
Primary Endpoints:
(1) Addenbrooke's Cognitive Examination—revised (ACE-R) and (2) Functional Activities Questionnaire [FAQ] or MRI (with Bonferroni Holme correction)
Secondary Endpoints:
Frontotemporal Dementia Rating Scale (FRS); Alzheimer's Disease Cooperative Society-Clinical Global Impression of Change [ADCS-CGIC]; Unified Parkinson's Disease Rating Scale (UPDRS Parts II and III, for safety).
Exploratory Endpoints:
ACE-III, as ACE-R now withdrawn; MMSE; Effect of LMTM in subjects with known genetic mutations associated with bvFTD Example 5—Power Analysis and Sample Size ACE-R was chosen as the primary end-point for the power calculation. However a further requirement was for cases to have MRI evidence of atrophy (≥Kipps 2), since cases with Kipps <2 and abnormal PET were unlikely to progress over 12 m (Mioshi et al. (2006) Int J Geriat Psych 21:1078-1085; Kipps Neurology (2008) 70:2046-2052).

Assuming ACE-R total score change from baseline to week 52 of 13.4±13.8.

With a sample of 180 (90 per treatment arm), for an estimated 50% reduction in projected decline (6.7 units), there would be 90% power to detect a treatment different of 6.7 units (or 50% reduction in projected decline) two-sided significance level of 0.05.

Example 6—Principal Inclusion Criteria

1 Diagnosis of probable bvFTD according to the International Consensus Criteria for bvFTD (Rascovsky et al., 2011, Sensitivity of revised diagnostic criteria for the behavioural variant of frontotemporal dementia. Brain 134:2456-2477)

2 Centrally rated frontotemporal atrophy score of 2 or greater (Kipps et al., 2007, Clinical significance of lobar atrophy in frontotemporal dementia: application of an MRI visual rating scale. Dementia Geriat. Cognit. Disord. 23:334-342)

3 MMSE ≥20 at the Screening Visit

4 Age <80 years at the Screening visit

5 Modified Hachinski ischemic score of ≤4 at the Screening visit

6 Informant/caregiver (≥2 hours per day, ≥3 days per week)

7 AD-labelled treatments (acetylcholinesterase inhibitors or memantine), where taken, started ≥3 months, with a stable dose ≥6 weeks prior to screening Example 7—ITT Population Initially 369 patients were assessed for eligibility. Of these 149 failed screening, with 75% excluded at pre-screen and 25% excluded at screen. This left 220 patients enrolled and randomised.

Figure 2:
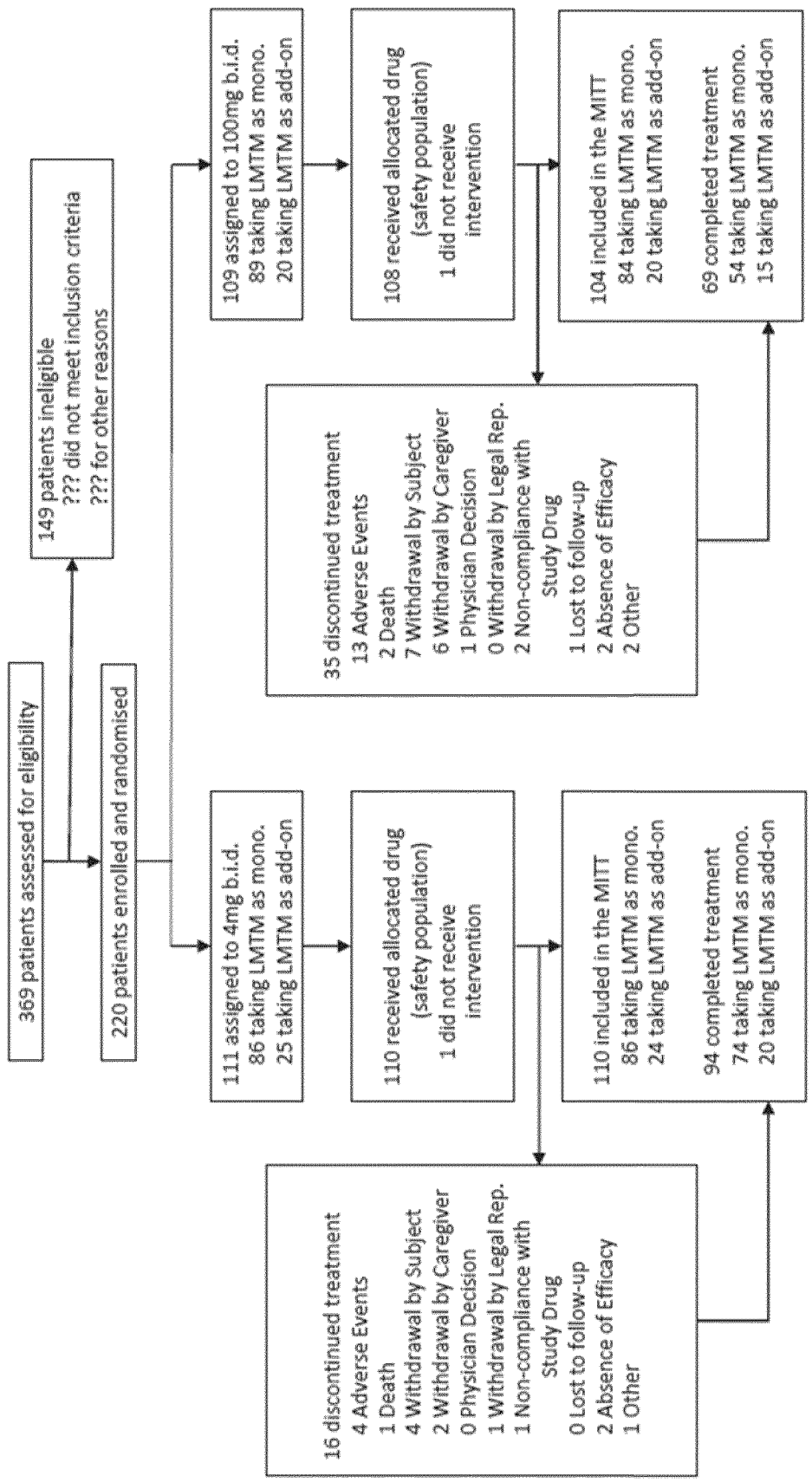

FIG. 2 shows the overall study disposition.

The demographics of the ITT population were as follows:

|  | Control (4 mg b.i.d.) (N = 111) | LMTM (100 mg b.i.d.) (N = 109) |
|---|---|---|
| Age (years) | | |
| Mean (SD) | 63.1 (7.35) | 63.6 (7.52) |
| Median (range) | 63.0 (43-78) | 64.0 (42-79) |
| Sex | | |
| Male | 67 (60.4%) | 71 (65.1%) |
| Female | 44 (39.6%) | 38 (34.9%) |
| Race | | |
| White | 102 (91.9%) | 99 (90.8%) |
| Other | 9 (8.1%) | 10 (9.2%) |

The baseline disease characteristics of the ITT population were as follows:

|  | Control (4 mg b.i.d.) (N = 111) | LMTM (100 mg b.i.d.) (N = 109) |
|---|---|---|
| Years Since Diagnosis | | |
| Mean (SD) | 1.81 (2.187) | 1.98 (2.456) |
| Median (range) | 0.93 (0.0-14.9) | 1.14 (0-17.6) |
| Kipps Stage n (%) | | |
| 2 | 37 (33.6%) | 40 (38.5%) |
| 3 | 55 (50.0%) | 45 (43.3%) |
| 4 | 18 (16.4%) | 19 (18.3%) |
| Severity Category by MMSE n (%) | | |
| >26 | 37 (33.6%) | 43 (41.3%) |
| 20-26 | 74 (66.4%) | 66 (58.7%) |
| Mutations in Coding Regions of Tau or TDP-43 Genes | | |
| Present/Absent | 1/26 | 0/29 |

Example 8—Primary Analysis Model

Figure 3:
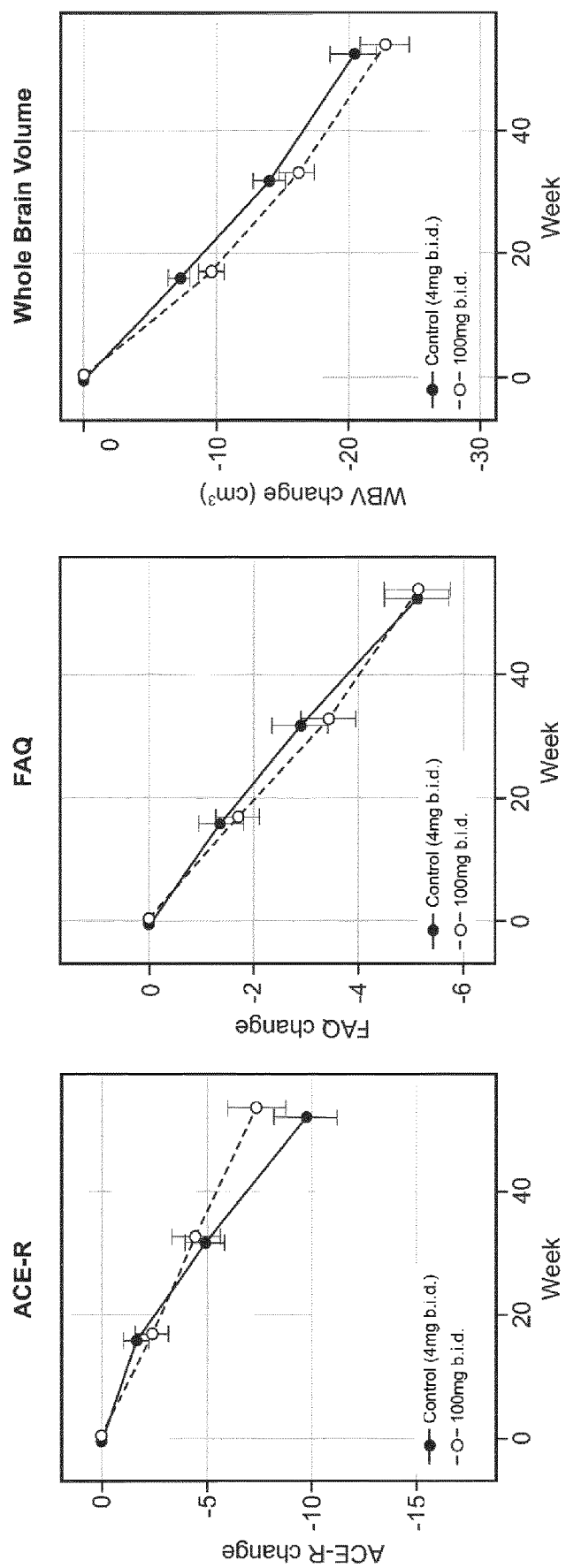
FIG. 3 shows the changes in the primary analysis models for ACE-R, FAQ and Whole Brain Volume. No difference between the two MT-compound dosages (LMTM at 4 mg b.i.d. and 100 mg b.i.d) was detected.

The primary analysis models for ACE-R, FAQ and Whole Brain Volume showed no difference between 4 mg b.i.d. and 100 mg b.i.d. This is shown in FIG. 3.

There was also no difference between 4 mg b.i.d. and 100 mg b.i.d. on ADCS-CGIC, FRS, MMSE, UPDRS (safety outcome)

One possible explanation for this is that both 4 mg b.i.d. and 100 mg b.i.d. have similar efficacy, which is consistent with the separate results seen in a phase 3 trial in mild to moderate AD patient to test the safety and efficacy of LMTM [data not shown].

Figure 4:
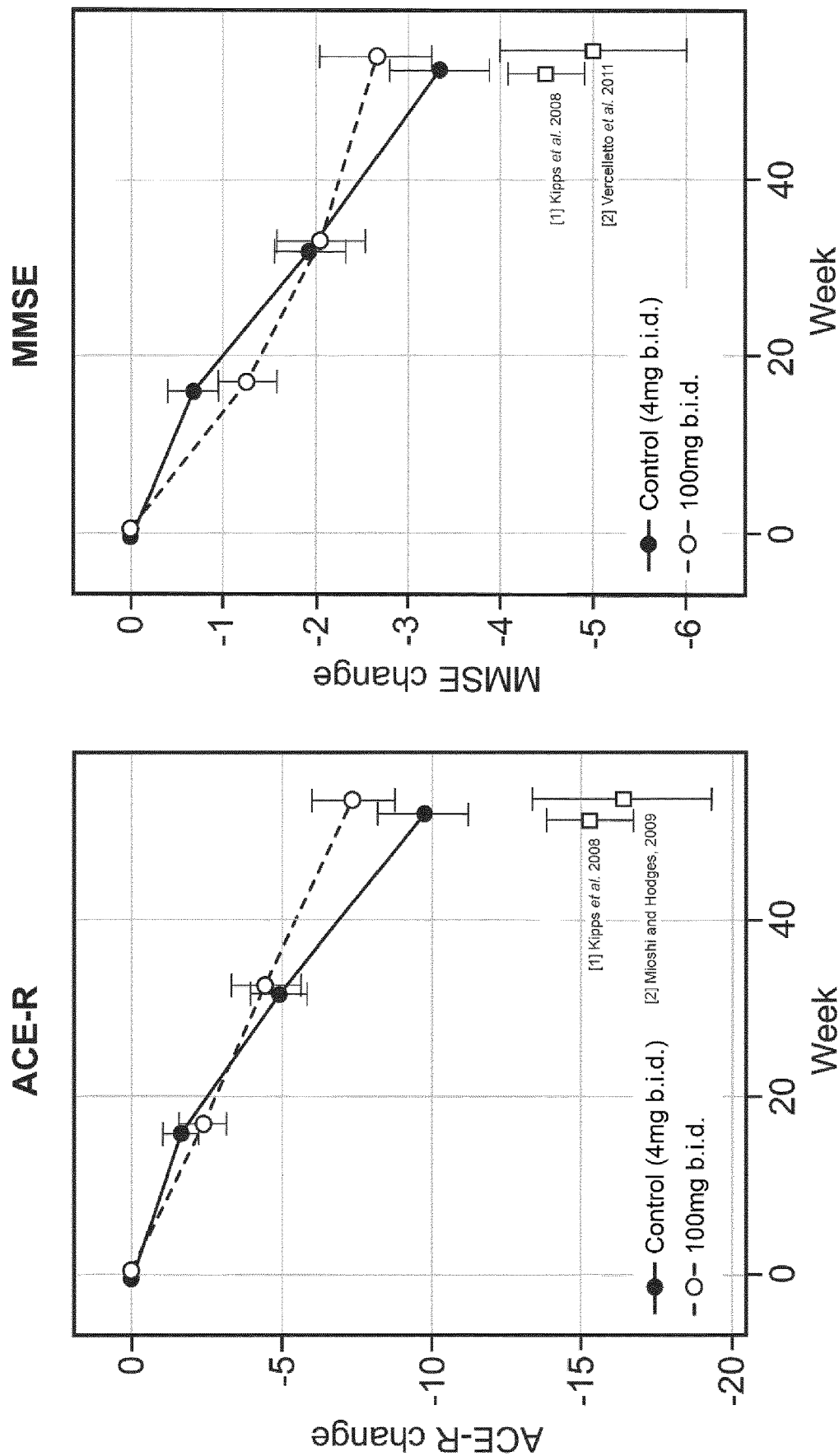
FIG. 4 shows that the decline seen on ACE-R and MMSE at 4 mg b.i.d. and 100 mg b.i.d. was significantly less than historical controls.

That conclusion is supported by the observations that the decline seen on ACE-R and MMSE at 4 mg b.i.d. and 100 mg b.i.d. was significantly less than historical controls. This is shown in FIG. 4 (references as follows: Kipps, C M, Nestor, P J, Dawson, C E, Mitchell, J, Hodges, J R (2008) Measuring progression in frontotemporal dementia: Implications for therapeutic interventions. Neurology 70:2046-

2052; Mioshi, E, Hodges, J R (2009) Rate of change of functional abilities in frontotemporal dementia. Dementia Geriat. Cognit. Disord. 28:419-426; Vercelletto, M, Boutoleau-Bretonniere, C, Volteau, C, Puel, M, Auriacombe, S et al. (2011) Memantine in Behavioral Variant Frontotemporal Dementia: Negative Results. J Alzheimers Dis 23:749-759). and the Table below.

|  | Baseline MMSE | | | 12 month change in ACE-R | | |
| --- | --- | --- | --- | --- | --- | --- |
|  | Historical | Present study | p-value | Historical | Present study (4/100 mg bd) | p-value |
| Kipps et al. (2008) | 25.0 ± 0.7 | 24.6 ± 0.2 | 0.6523 | 15.3 ± 1.4 | 10.4 ± 1.4 | 0.0067 |
|  |  |  |  |  | 10.7 ± 1.4 | 0.0184 |
| Mioshi & Hodges (2009) | 25.6 ± 2.81 | 24.6 ± 0.2 | 0.3609 | 16.4 ± 3.1 | 10.4 ± 1.4 | 0.0389 |
|  |  |  |  |  | 10.7 ± 1.4 | 0.0469 |

|  | Baseline MMSE | | | 12 m change in MMSE | | |
| --- | --- | --- | --- | --- | --- | --- |
|  | Historical | Present study | p-value | Historical | Present study (4/100 mg bd) | p-value |
| Kipps et al. (2008) | 25.0 ± 0.7 | 24.6 ± 0.2 | 0.6523 | 24.5 ± 0.4 | 3.4 ± 0.5 | 0.0429 |
|  |  |  |  |  | 3.0 ± 0.7 | 0.0314 |
| Vercelletto et al. (2011) | 25.0 ± 0.7 | 24.5 ± 0.2 | 0.5625 | 5.0 ± 1.0 | 3.4 ± 0.5 | 0.0762 |
|  |  |  |  |  | 3.0 ± 0.7 | 0.0507 |

Example 9—Effect of Co-Medication with AD Treatments

The effect of co-medication with symptomatic AD treatments which modify synaptic neurotransmission in the brain (acetylcholinesterase inhibitors or the NMDA antagonist "memantine") was assessed. For brevity these treatments may be referred to as "AChEI/Mem" below.

The total number of subjects analysed was 214, of which 44 had been receiving AChEI/Mem (ie 21%). The subjects were split in terms of severity, with 52, 82 and 80 having MMSE values of <22, 22-26 and >26, respectively. Geographically, these patients were from Europe (87%), United States (80%) or Asia (13%).

| Variable for mITT | | N | % |
| --- | --- | --- | --- |
| AD ConMeds | with AChEI/Mem | 44 | 21% |
|  | without AChEI/Mem | 170 | 79% |
| Severity | MMSE <22 | 52 | 24% |
|  | MMSE 22-26 | 82 | 38% |
|  | MMSE >26 | 80 | 38% |
| Geographic | Europe | 100 | 47% |
|  | Americas | 86 | 40% |
|  | Asia | 28 | 13% |

Unexpectedly, AD-comedication status and severity were found to be significant covariates.

Therefore further prespecified post hoc exploratory analyses were undertaken taking account of these covariates. These are described below, and indicated that there are significant benefits (as measured on ACE-R) in patients taking LMTM in combination with off-label AD treatments (AChEI/Mem) versus LMTM alone. There also appeared to be directionally supportive benefits on FAQ, MMSE and fronto-temporal volume.

Figure 5:
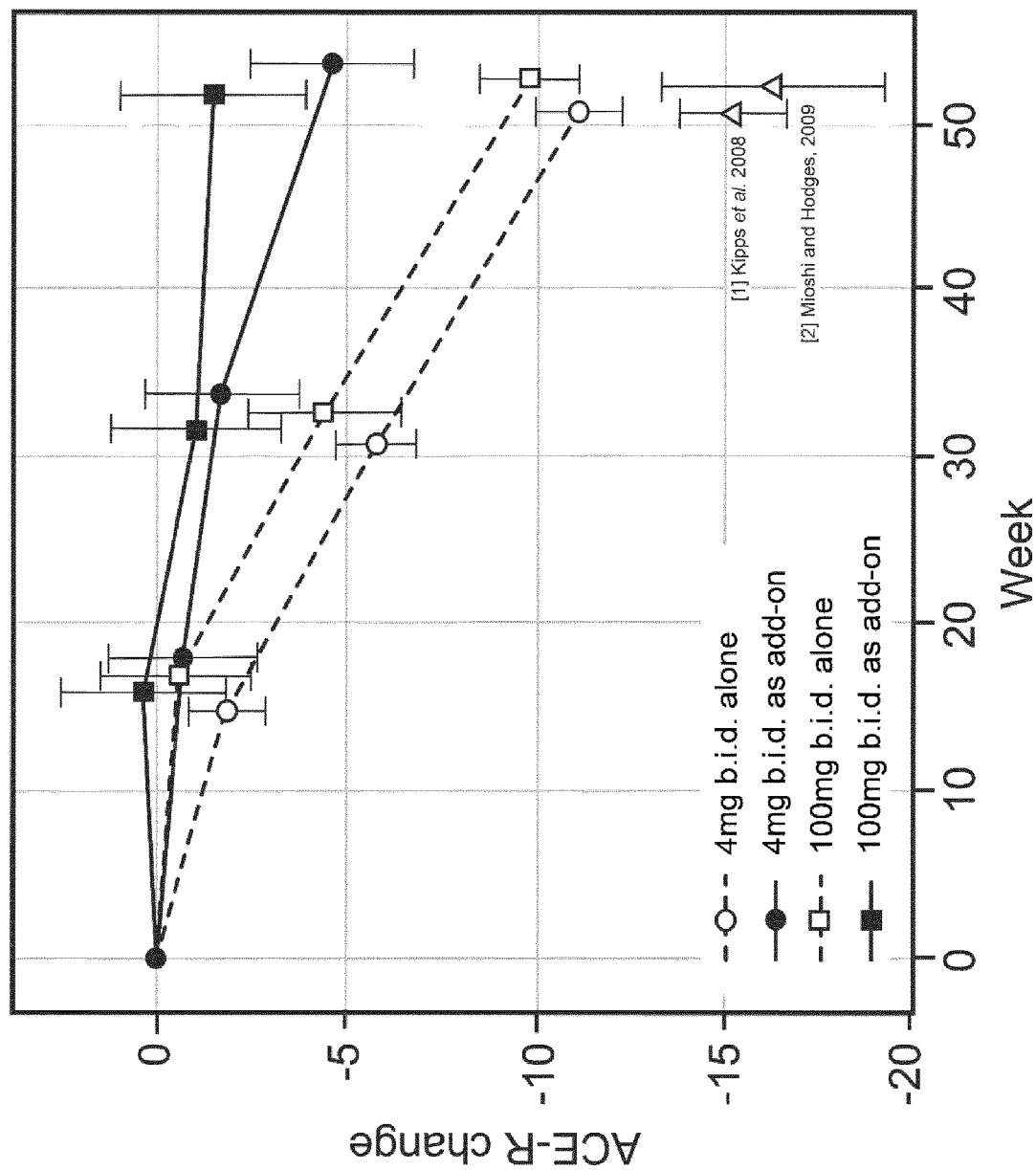
FIG. 5 shows the ACE-R analysis: ANCOVA model for the effects if the MT compound, taking account of AD-comedication status.

FIG. 5 shows the ACE-R analysis: ANCOVA model taking account of AD-comedication status and severity. The data is shown in the Table below.

| (Comparisons wrt 4 mg b.i.d. alone) | Treatment effect mean (se) | p-value |
| --- | --- | --- |
| 4 mg b.i.d. as add-on | 6.52 (2.42) | 0.0073 |
| 100 mg b.i.d. as add-on | 9.69 (2.73) | 0.0004 |
| 100 mg b.i.d. alone | 1.35 (1.71) | 0.4300 |

Figure 6:
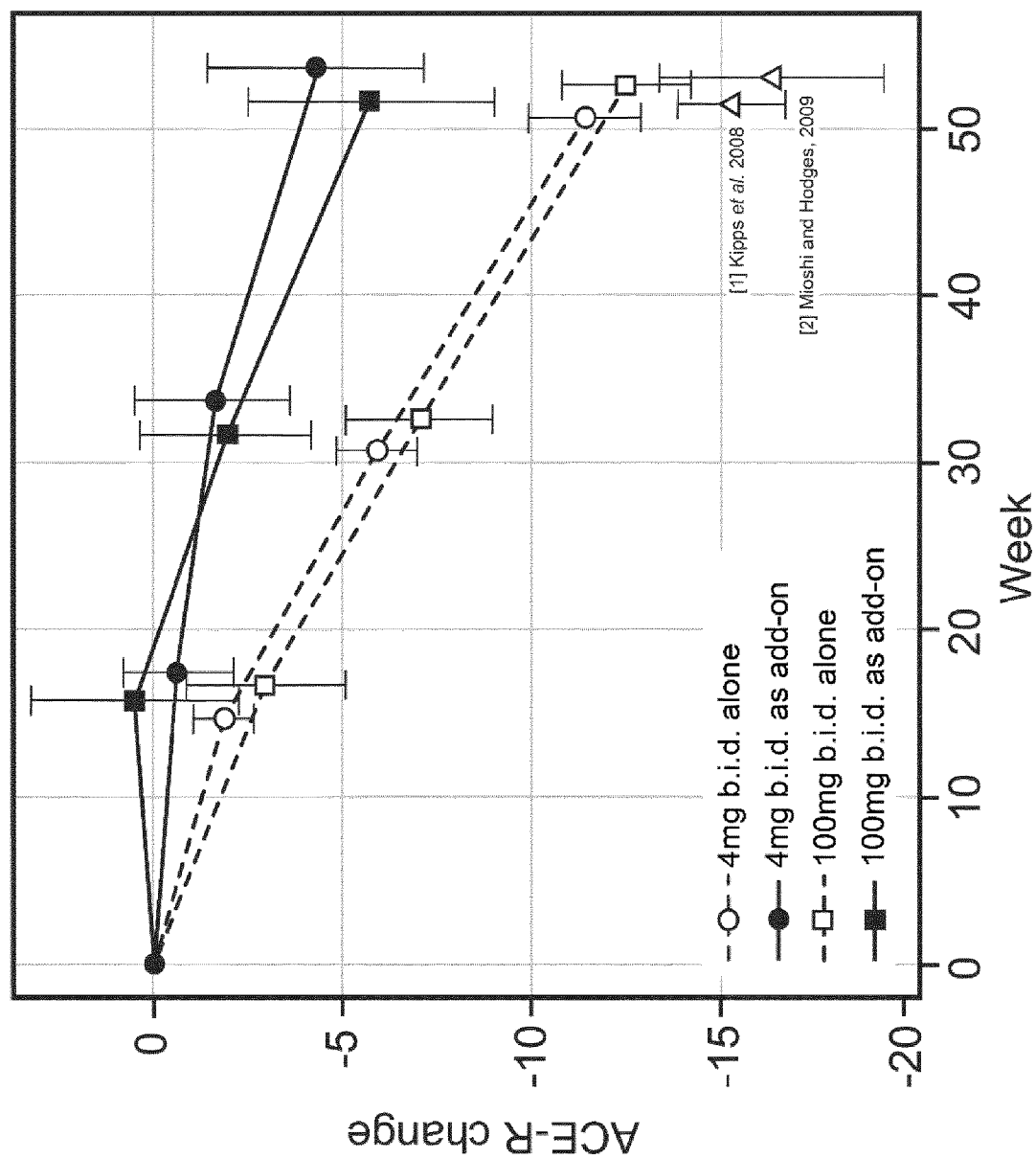
FIG. 6 shows the ACE-R analysis: MMRM model for the effects if the MT compound, taking account of AD-comedication status.

FIG. 6 shows the ACE-R analysis: MMRM model taking account of AD-comedication status and severity. The data is shown in the Table below:

| (Comparisons wrt 4 mg b.i.d. alone) | Treatment effect mean (se) | p-value |
| --- | --- | --- |
| 4 mg b.i.d. as add-on | 7.17 ± 3.25 | 0.0273 |
| 100 mg b.i.d. as add-on | 5.65 ± 3.57 | 0.1132 |
| 100 mg b.i.d. alone | −1.12 ± 2.28 | 0.6228 |

Figure 7:
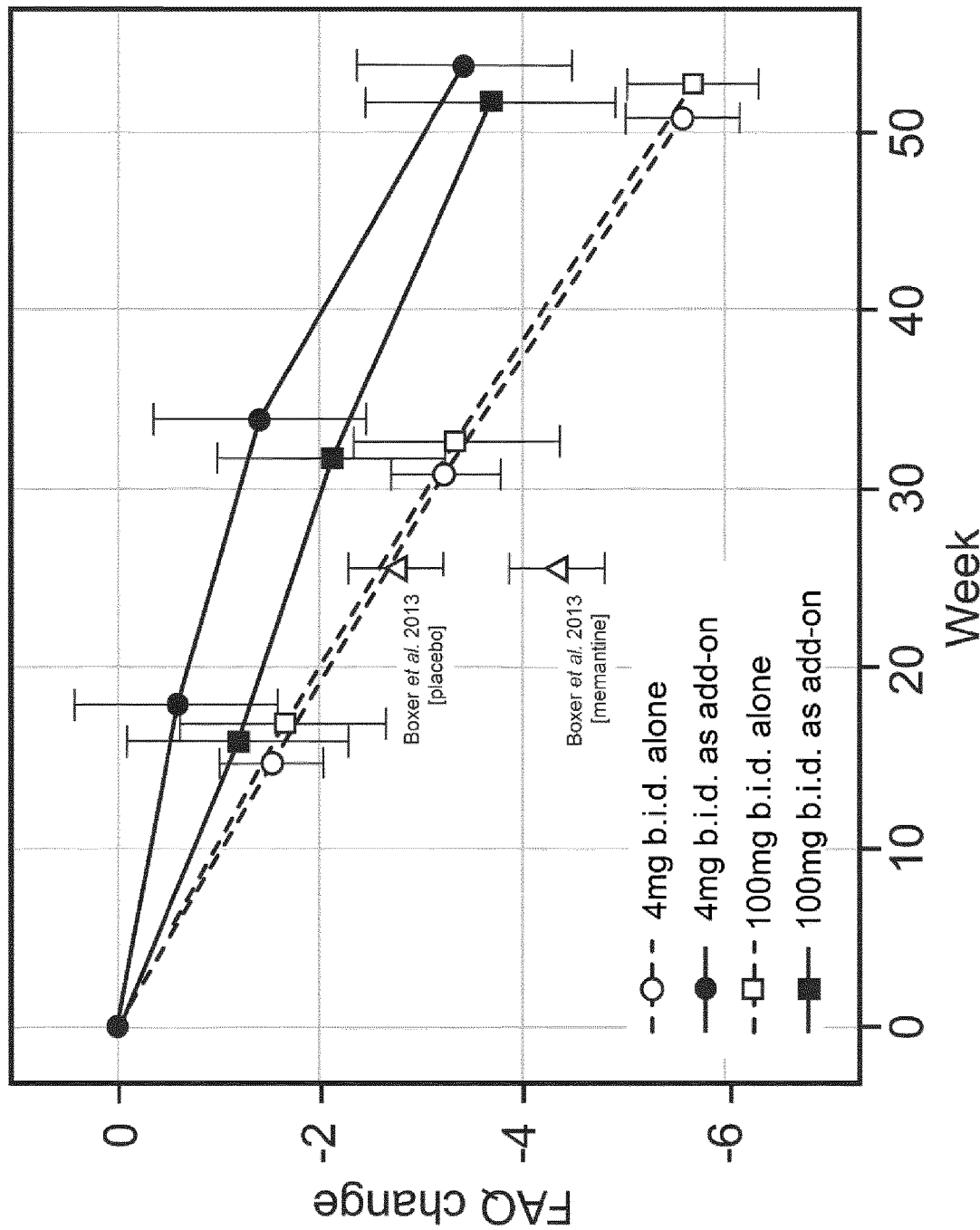
FIG. 7 shows the FAQ analysis: ANCOVA model for the effects if the MT compound, taking account of AD-comedication status.

FIG. 7 shows FAQ analysis: ANCOVA model taking account of AD-comedication status and severity. The data is shown in the Table below:

| (Comparisons wrt 4 mg b.i.d. alone) | Treatment effect mean (se) | p-value |
| --- | --- | --- |
| 4 mg b.i.d. as add-on | 2.15 ± 1.21 | 0.0777 |
| 100 mg b.i.d. as add-on | 1.90 ± 1.37 | 0.1649 |
| 100 mg b.i.d. alone | −0.11 ± 0.87 | 0.9017 |

Figure 8:
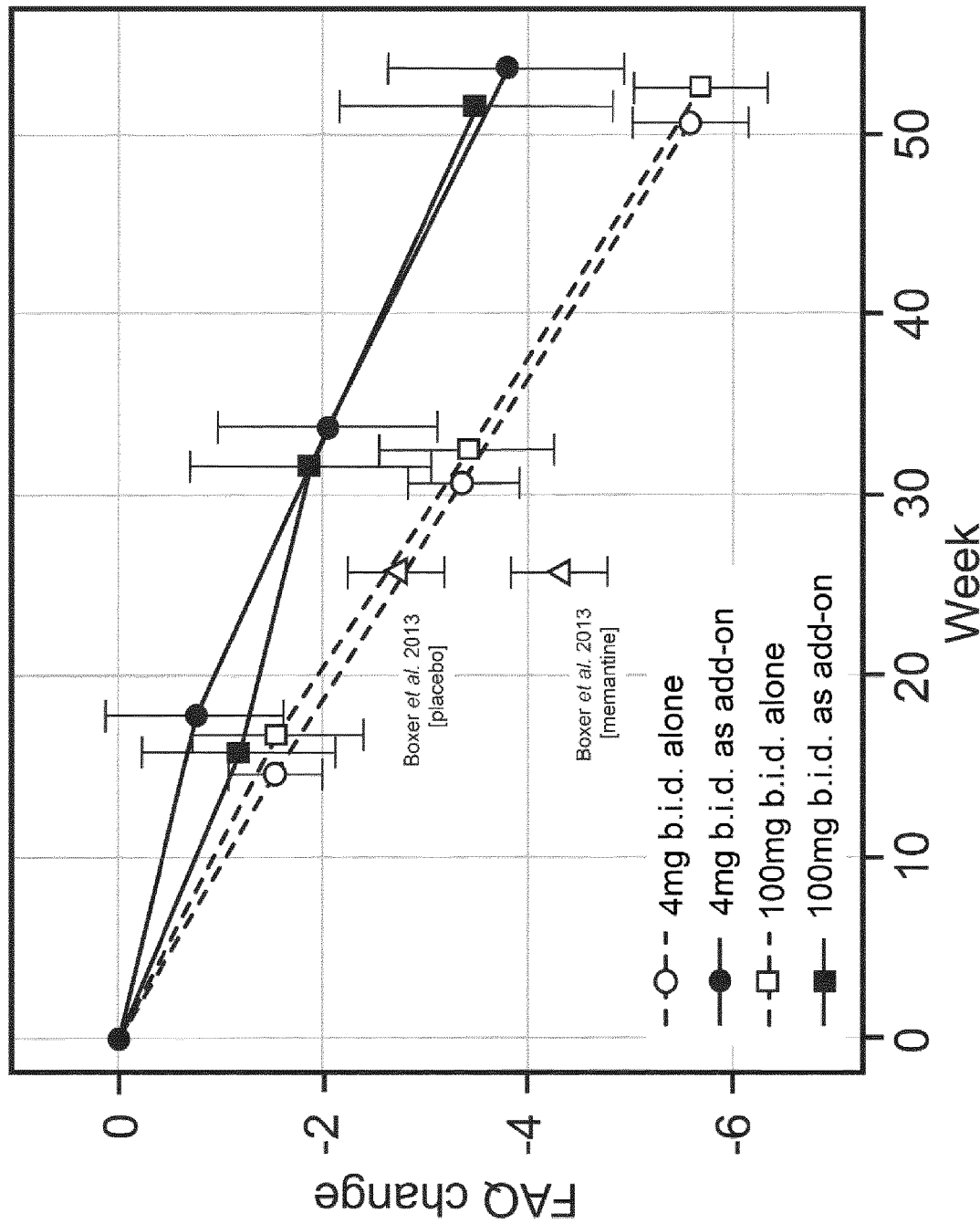
FIG. 8 shows the FAQ analysis: MMRM model for the effects if the MT compound, taking account of AD-comedication status.

FIG. 8 shows FAQ analysis: MMRM model taking account of AD-comedication status and severity. The data is shown in the Table below:

| (Comparisons wrt 4 mg b.i.d. alone) | Treatment effect mean (se) | p-value |
| --- | --- | --- |
| 4 mg b.i.d. as add-on | 2.08 ± 1.31 | 0.1132 |
| 100 mg b.i.d. as add-on | 2.36 ± 1.45 | 0.1039 |
| 100 mg b.i.d. alone | −0.03 ± 0.92 | 0.9747 |

Figure 9:
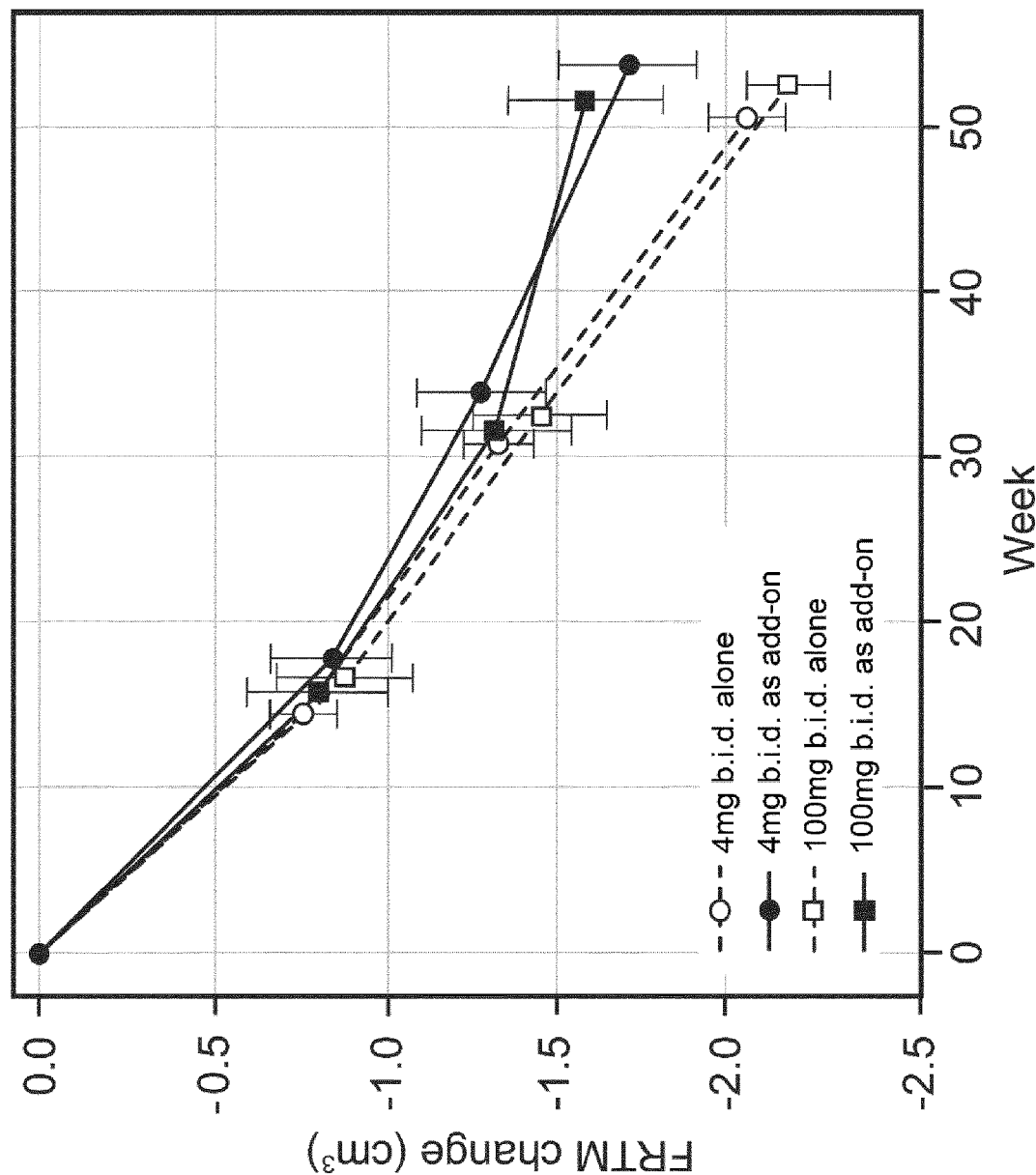
FIG. 9 shows the Fronto-temporal volume analysis: ANCOVA model for the effects if the MT compound, taking account of AD-comedication status.

FIG. 9 shows Fronto-temporal volume analysis: ANCOVA model taking account of AD-comedications and severity. The data is shown in the Table below:

| (Comparisons wrt 4 mg b.i.d. alone) | Treatment effect mean (se) | p-value |
|---|---|---|
| 4 mg b.i.d. as add-on | 356 (237) | 0.1337 |
| 100 mg b.i.d. as add-on | 481 (258) | 0.0628 |
| 100 mg b.i.d. alone | −98 (173) | 0.5722 |

Figure 10:
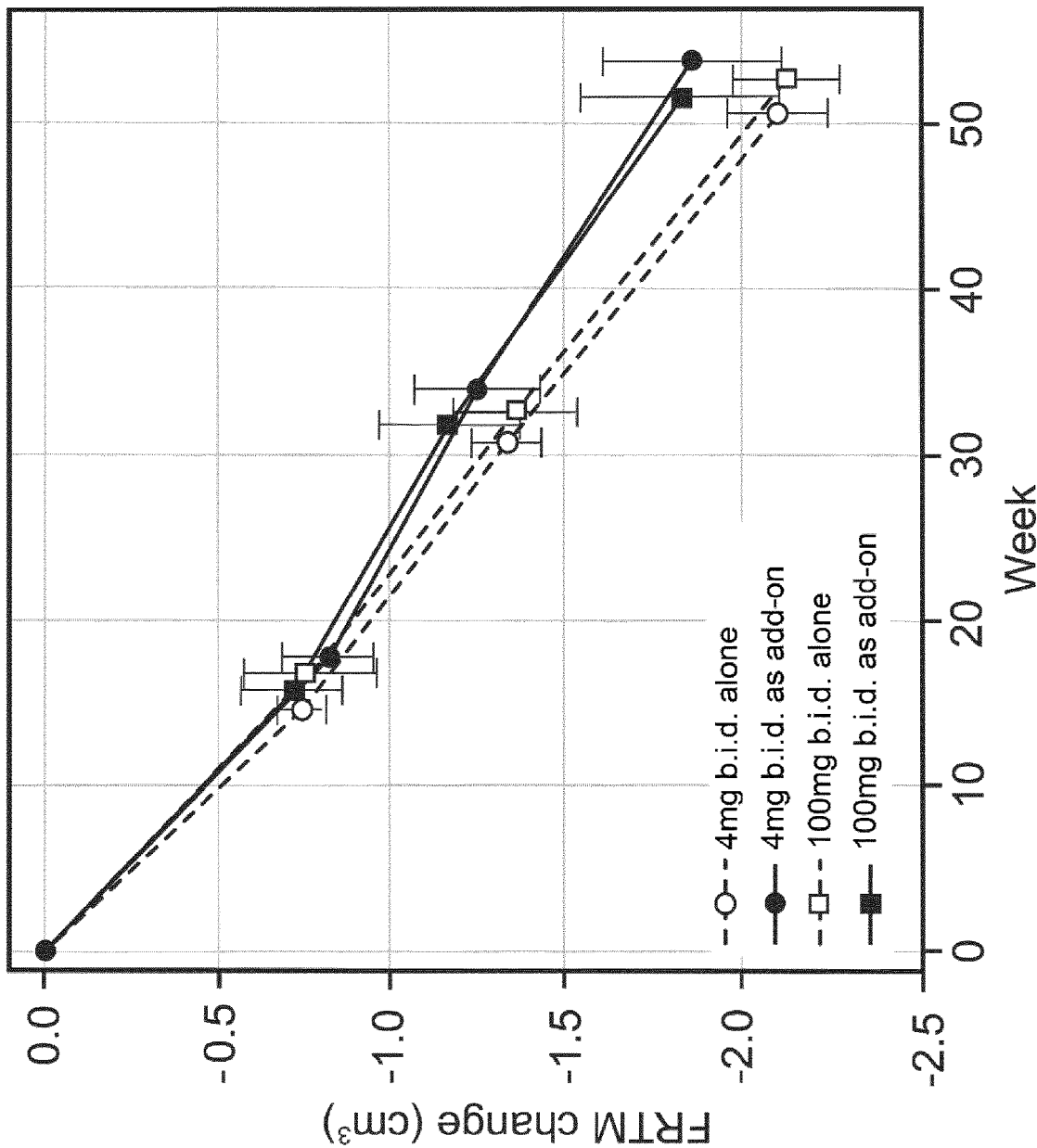
FIG. 10 shows the Fronto-temporal volume: MMRM model for the effects if the MT compound, taking account of AD-comedication status.

FIG. 10 shows Fronto-temporal volume analysis: MMRM model taking account of AD-comedications and severity. The data is shown in the Table below:

| (Comparisons wrt 4 mg b.i.d. alone) | Treatment effect mean (se) | p-value |
|---|---|---|
| 4 mg b.i.d. as add-on | 240 (291) | 0.4110 |
| 100 mg b.i.d. as add-on | 278 (313) | 0.3745 |
| 100 mg b.i.d. alone | −4 (207) | 0.9831 |

The Table below shows Baseline comparison of demographic and clinical parameters in subjects taking and not-taking AD-treatments off-label:

| | bvFTD (not taking) | bvFTD (taking) | p-value |
|---|---|---|---|
| Age | 63.6 ± 1.0 | 63.2 ± 0.6 | 0.7380 |
| Sex | 34% female | 45% female | 0.2236 |
| Time since diagnosis | 1.7 ± 0.2 | 2.5 ± 0.4 | 0.0856 |
| Region (North America, Asia, EU) | 39%, 13%, 48% | 45%, 14%, 41% | 0.6726 |
| ACE-R | 69.2 ± 1.1 | 67.1 ± 2.3 | 0.4817 |
| FAQ | 13.5 ± 0.6 | 13.7 ± 1.1 | 0.8666 |
| MMSE | 24.6 ± 0.3 | 23.9 ± 0.6 | 0.2960 |
| FRS - total | 0.47 ± 0.02 | 0.46 ± 0.05 | 0.8450 |
| FRS - behavioural items | 0.52 ± 0.02 | 0.50 ± 0.04 | 0.6928 |
| FRS - functional items | 0.45 ± 0.02 | 0.44 ± 0.03 | 0.8161 |

The Table below shows there are no significant differences shown by a Baseline comparison of brain volumes in subjects taking and not-taking AD-treatments off-label

| | bvFTD (not taking) (n = 164) | bvFTD (taking) (n = 43) | p-value |
|---|---|---|---|
| Whole brain volume (cm$^3$) | 975 (10) | 937 (18) | 0.0745 |
| Lateral ventricular volume (cm$^3$) | 53.3 (1.7) | 50.9 (4.0) | 0.5809 |
| Hippocampal volume | 3.12 (0.05) | 3.06 (0.11) | 0.6309 |
| Anterior cingulate volume | 3.52 (0.06) | 3.47 (0.13) | 0.6874 |
| Posterior cingulate volume | 2.61 (0.04) | 2.58 (0.08) | 0.7238 |

Example 10—Conclusions from Trial

Although the primary outcomes (based on the pre-specified end-points) were not achieved, a number of observations can be made about the results.

Firstly, the safety profile (not shown) was similar to that seen in other studies using MT compounds and raised no major concerns Secondly, there was less cognitive decline (as assessed using ACE-R) seen at 4 mg b.i.d. and 100 mg b.i.d. than would have been predicted from historical studies. This could be explained if both the 4 mg b.i.d. (the "control" arm) and 100 mg b.i.d. (the "active" arm) demonstrated efficacy.

Thirdly, AD-comedication status and severity found to be significant covariates. Further (prespecified) exploratory post hoc analyses taking account of these covariates showed significant benefits on ACE-R in patients taking LMTM in combination with off-label AD treatments (acetylcholinesterase inhibitors and/or memantine) versus LMTM alone. There also appeared to be directionally supportive benefits on FAQ, MMSE and fronto-temporal volume In summary, in the context of the FTD, there appear to be strong interaction effects between LMTM and AD treatments which modify synaptic neurotransmission in the brain. The results suggest that an unexpected benefit can be achieved in the treatment of an FTD when using MT compounds in combination with such treatments.

Example 11—Compatibility of MT Compounds and AD Treatments

The effect of combining tablets of galantamine, memantine, donepezil or rivastigmine independently with LMTM was studied and LMTM was analysed in the resultant mixture.

Figure 11:
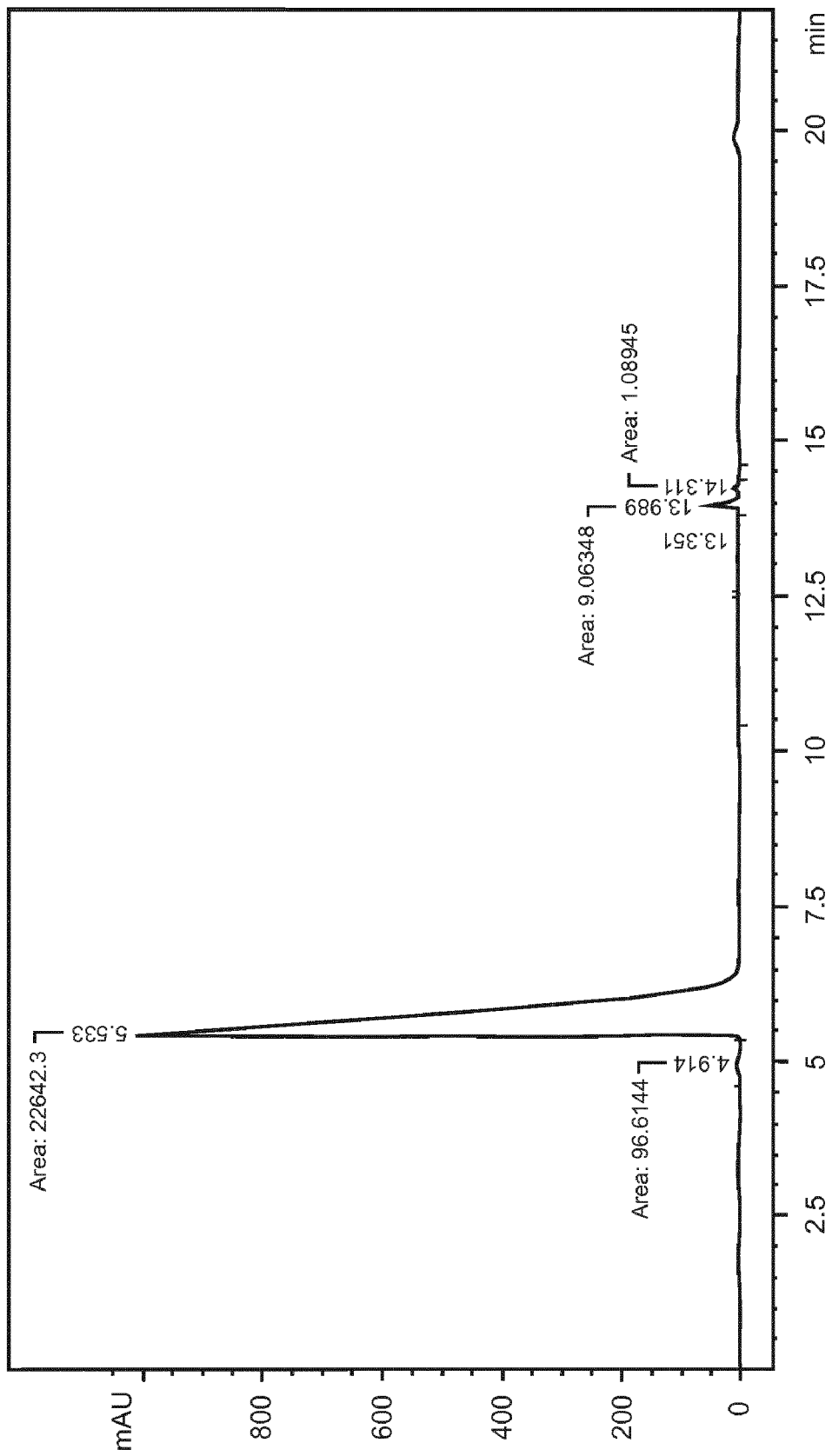
FIG. 11 shows an HPLC Chromatogram of LMTM with memantine, showing LMT at 5.5 minutes and MT at 14 minutes (see Example 11).

One LMTM tablet (100 mg) was added to a degassed 200 ml amber volumetric flask along with one prescription dose of each of the test drugs, as indicated in the table below, and 100 ml of diluent (degassed 0.1% formic acid). Flasks were given an argon headspace and shaken on a wrist action shaker for 40 minutes at 250 oscillations/min. Samples were then diluted to the graduation mark with diluent, given an argon headspace and inverted to mix. Subsamples of the resulting solution were centrifuged at 13,000 rpm for 5 minutes to remove any undissolved excipients and the supernatant placed in an amber HPLC vial and injected into a high performance liquid chromatography (HPLC) system (Agilent 1260) to separate LMT and MT. LMT and MT peaks were identified by absorbance at 255 nm with retention times of 5.5 and 14 minutes, respectively (FIG. 11). The recovery of LMT and MT in the experiments is shown in the table below.

| LMTM | Tablet Mix Addition | LMT (area) | MT (area) | LMT (% difference from control*) | MT (% difference from control*) |
|---|---|---|---|---|---|
| 100 mg LMTM | none | 22465.7 | 390.5473 | | |
| 100 mg LMTM | 12 mg galantamine | 22157.4 | 332.34845 | −1.37 | −14.90 |
| 100 mg LMTM | 10 mg memantine | 22642.3 | 336.01703 | 2.19 | 1.10 |
| 100 mg LMTM | 10 mg donepezil | 22058.4 | 313.9205 | −2.58 | −6.58 |
| 100 mg LMTM | 6 mg rivastigmine | 23302.4 | 320.62292 | 5.64 | 2.14 |

Less than 2% of the LMTM was found in the oxidised form following HPLC analysis. The amount of oxidised MT was not increased after mixing with any of the AChEIs or memantine. If LMTM were to reduce the AChEIs or memantine, then LMTM itself would become oxidised; this does not happen.

The experiments above illustrate that MT compounds can be combined with acetylcholinesterase inhibitors and/or memantine without apparent incompatibility.

The invention claimed is:
1. A method of treatment of an FTLD syndrome in a human subject, which method comprises administering to said subject:
   a first compound which is a methylthioninium (MT) compound in combination with
   a second compound, which second compound directly modifies synaptic neurotransmission in the brain,
   wherein the FTLD syndrome is selected from behavioral-variant frontotemporal dementia, primary progressive aphasia, and semantic dementia; and wherein the MT compound is a salt of:

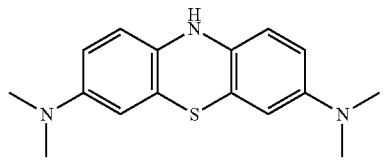

or a hydrate or solvate thereof, and
   wherein the second compound is either an acetylcholinesterase inhibitor or an NMDA receptor antagonist.
2. A method claim 1, wherein either:
   (a) the MT compound and the neurotransmission modifying compound are administered sequentially within 12 hours of each other;
   (b) the subject is pre-treated with the neurotransmission modifying compound prior to commencement of the treatment with the MT compound; or
   (c) the MT compound and the neurotransmission modifying compound are administered simultaneously, optionally within a single dosage unit.
3. A method as claimed in claim 1, wherein the MT compound is an LMTX compound of the following formula:

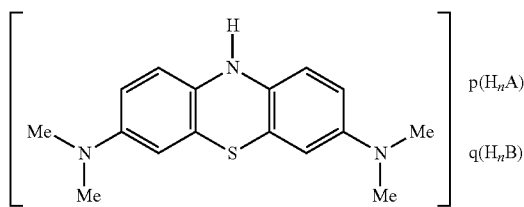

wherein each of $H_nA$ and $H_nB$ (where present) are protic acids which may be the same or different,
   and wherein p=1 or 2; q=0 or 1; n=1 or 2; (p+q)×n=2.
4. A method as claimed in claim 3, wherein the MT compound has the following formula:

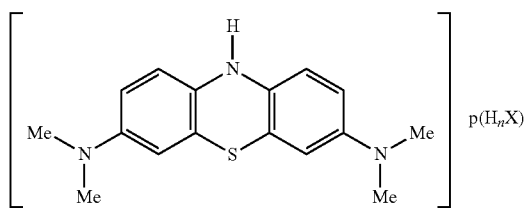

wherein each of $H_nX$ is a protic acid.

5. A method as claimed in claim 3, wherein the MT compound has the following formula and $H_2A$ is a di-protic acid:

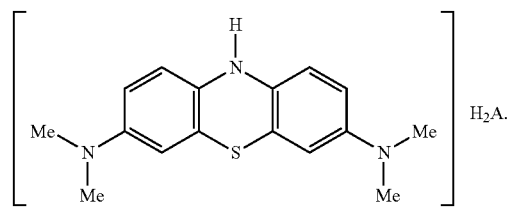

6. A method as claimed in claim 4, wherein the MT compound has the following formula and is a bis-monoprotic acid:

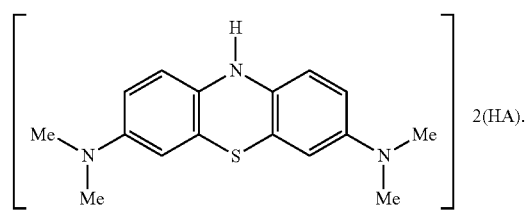

7. A method as claimed in claim 3, wherein the or each protic acid is an inorganic acid.
8. A method as claimed in claim 3, wherein the or each protic acid is an organic acid.
9. A method as claimed in claim 8, wherein the MT compound is LMTM:

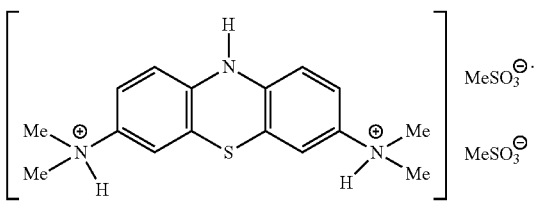

10. A method as claimed in claim 1, wherein the FTLD syndrome is FTLD with tau pathology or FTLD with TAR DNA-binding protein 43 pathology.
11. A method as claimed in claim 1, wherein the total daily dose of MT provided by the MT compound is from around any of 1 to 350 mg; 2 to 300 mg; 4 to 250 mg; 6 to 240 mg; 7 to 220 mg, or 3 to 70 mg.
12. A method as claimed in claim 1, wherein the total daily dose of MT provided by the MT compound is from around any of 0.5, 1, 1.5, 2, 2.5, 3, 3.5, 4 mg to around any of 5, 6, 7, 8, 9, 10, 11, 12, 13, 14, 15, 16, 17, 18, 19, 20 mg.

* * * * *